US011292790B2

(12) United States Patent
Perdew et al.

(10) Patent No.: US 11,292,790 B2
(45) Date of Patent: *Apr. 5, 2022

(54) NETWORK-CENTRIC SENSOR COVERAGE MANAGEMENT

(71) Applicant: Quixotic Holdings LLC, Tacoma, WA (US)

(72) Inventors: Matthew David Perdew, Anchorage, AK (US); Ryan Scott Luther, Tacoma, WA (US)

(73) Assignee: QUIXOTIC HOLDINGS, LLC, Fife, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/077,892

(22) Filed: Oct. 22, 2020

(65) Prior Publication Data

US 2021/0040082 A1 Feb. 11, 2021

Related U.S. Application Data

(63) Continuation of application No. 16/447,459, filed on Jun. 20, 2019, now Pat. No. 10,836,762.

(60) Provisional application No. 62/687,636, filed on Jun. 20, 2018.

(51) Int. Cl.
| | | |
|---|---|---|
| C07D 455/06 | (2006.01) |
| A61K 31/4745 | (2006.01) |
| A61K 47/64 | (2017.01) |
| G01S 13/91 | (2006.01) |
| G08G 5/00 | (2006.01) |
| H04B 7/06 | (2006.01) |
| H04B 7/08 | (2006.01) |
| H04B 7/26 | (2006.01) |

(52) U.S. Cl.
CPC ........ *C07D 455/06* (2013.01); *A61K 31/4745* (2013.01); *A61K 47/646* (2017.08); *G01S 13/91* (2013.01); *G08G 5/0008* (2013.01); *H04B 7/0617* (2013.01); *H04B 7/086* (2013.01); *H04B 7/2606* (2013.01)

(58) Field of Classification Search
CPC .............. C07D 455/06; A61K 47/646; A61K 31/4745; G01S 13/91; G08G 5/0008; H04B 7/0617; H04B 7/086; H04B 7/2606
USPC ........................ 455/652.1, 272–279; 343/850
See application file for complete search history.

(56) References Cited

U.S. PATENT DOCUMENTS

| | | | | |
|---|---|---|---|---|
| 9,471,063 B2 * | 10/2016 | Ouyang | ............... | A01D 34/008 |
| 9,788,282 B2 * | 10/2017 | Neves | ................... | H04W 52/24 |
| 9,918,234 B2 * | 3/2018 | Zerick | .................. | H04W 24/02 |
| 9,955,436 B2 * | 4/2018 | Neves | ................... | H04W 16/28 |
| 10,178,509 B1 * | 1/2019 | Perdew | ................ | H04W 4/029 |

(Continued)

*Primary Examiner* — Hai V Nguyen
(74) *Attorney, Agent, or Firm* — Seed IP Law Group LLP

(57) ABSTRACT

Embodiments described herein are directed to employing an aggregation of participant sensor coverage areas to determine if there are missing coverage areas or unwanted overlapping coverage areas. If there are missing coverage areas, then at least one participant is instructed to modify its sensor coverage area to at least partially cover the missing coverage area. Conversely, if at least one participant has a sensor that is providing unwanted overlap of other sensor coverage areas, then that participant may be instructed to stop using that sensor, utilize that sensor for other data transmission purposes, or modify the coverage area to be non- or less-overlapping.

20 Claims, 13 Drawing Sheets

(56) References Cited

U.S. PATENT DOCUMENTS

| | | | |
|---|---|---|---|
| 10,321,330 B2* | 6/2019 | Zerick | H04W 16/26 |
| 10,419,103 B1* | 9/2019 | Perdew | H04W 4/023 |
| 10,462,609 B1* | 10/2019 | Carroll | H04W 4/029 |
| 10,836,762 B2* | 11/2020 | Perdew | G08G 5/0008 |
| 2006/0176160 A1* | 8/2006 | Zoratti | G08G 1/16 340/435 |
| 2010/0225764 A1* | 9/2010 | Nizko | G01S 7/4004 348/152 |
| 2013/0099943 A1* | 4/2013 | Subramanya | B60Q 9/002 340/933 |
| 2013/0259381 A1* | 10/2013 | Srinivasan | G06K 9/00771 382/192 |
| 2014/0051446 A1* | 2/2014 | Rose | H04W 52/0206 455/436 |
| 2015/0141027 A1* | 5/2015 | Tsui | H04W 24/02 455/452.1 |
| 2016/0188755 A1* | 6/2016 | Gonzalez-Banos | G06F 30/20 703/1 |
| 2016/0242043 A1* | 8/2016 | Dong | H04W 16/20 |
| 2016/0313736 A1* | 10/2016 | Schultz | G08G 5/0039 |
| 2016/0371865 A1* | 12/2016 | Jedwab | G06T 11/203 |
| 2017/0156119 A1* | 6/2017 | Neves | H04W 52/24 |
| 2017/0230916 A1* | 8/2017 | Stein | H04W 4/38 |
| 2017/0257779 A1* | 9/2017 | Zerick | H04W 24/02 |
| 2018/0035391 A1* | 2/2018 | Neves | H04W 52/386 |
| 2018/0059213 A1* | 3/2018 | Wallstedt | G01S 7/021 |
| 2018/0199210 A1* | 7/2018 | Zerick | H04W 64/003 |
| 2018/0342102 A1* | 11/2018 | Hovis | G06K 9/00791 |
| 2018/0362157 A1* | 12/2018 | Teetzel | B64C 39/024 |
| 2019/0098457 A1* | 3/2019 | Perdew | H04W 4/023 |
| 2019/0098458 A1* | 3/2019 | Perdew | H04B 7/18506 |
| 2019/0115657 A1* | 4/2019 | Hwang | H04B 7/0615 |
| 2019/0265724 A1* | 8/2019 | Sheng | G05D 1/0088 |
| 2019/0277941 A1* | 9/2019 | Hehn | H04W 4/026 |
| 2019/0309975 A1* | 10/2019 | Salem | F24F 11/72 |
| 2019/0331792 A1* | 10/2019 | Raillon | G01S 15/42 |
| 2019/0349070 A1* | 11/2019 | Perdew | H04B 7/18504 |

* cited by examiner

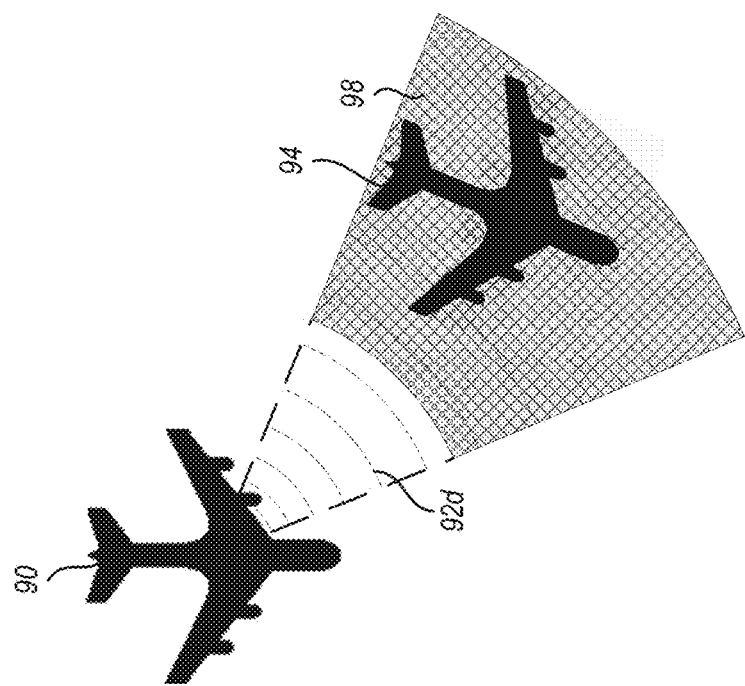

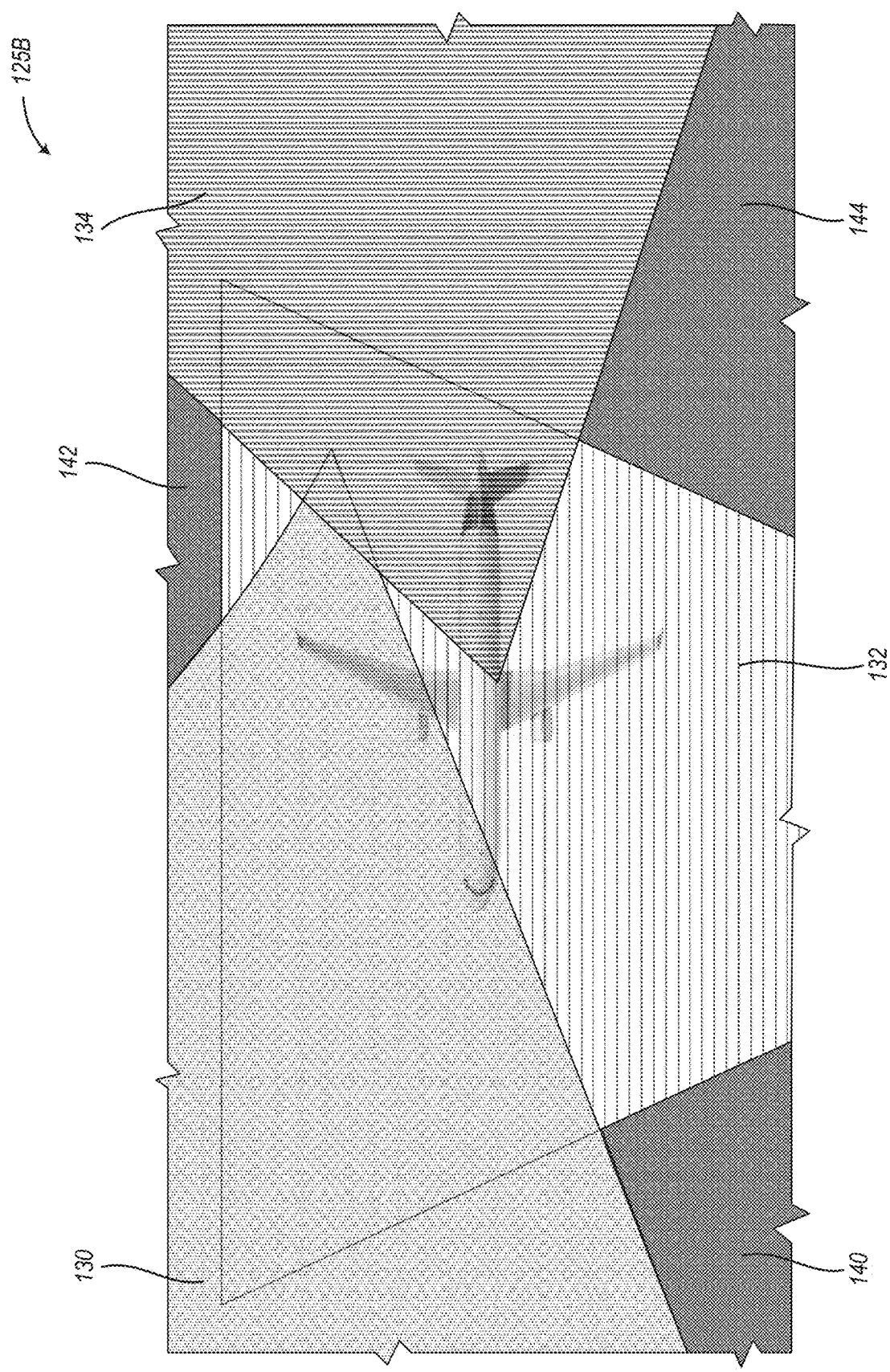

NETWORK-CENTRIC SENSOR COVERAGE MANAGEMENT

BACKGROUND

Technical Field

The present disclosure relates generally to sensor and information distribution management and, more particularly, to utilizing aggregated information from multiple sensor of participant devices to reduce overlapping sensor coverage.

Description of the Related Art

Airplanes typically rely on radar or GPS information to track other airplanes. Some airplanes, however, may be flying in an area with poor or unreliable radar coverage. Similarly, some airplanes may not broadcast their current location to other airplanes. As a result, the radar and GPS information may not present a complete picture of all the airplanes in a given area, and thus create a dangerous situation in which airplanes may be flying near or towards one another without knowing.

At the same time, mobile communication devices, such as smart phones, have become a very integral part in many people's lives. And the number of mobile communication devices in use, and people's reliance thereon, continues to grow. For example, many people have a need or expect to be able to connect to the Internet in a variety of different locations, including on commercial airlines. Many commercial airlines rely on satellite communication networks to provide its passengers with Internet access. However, these communication networks are often slow and have limited bandwidth capabilities. It is with respect to these and other considerations that the following disclosure addresses.

BRIEF DESCRIPTION OF THE SEVERAL VIEWS OF THE DRAWINGS

Non-limiting and non-exhaustive embodiments are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings:

FIGS. 4A-4B illustrate context diagrams of using directional signaling and scanning to provide directional communication between participants in accordance with embodiments described herein;

FIGS. 6A-6E illustrates context diagrams illustrating a use-case example of utilizing directional sensors along with sensor coverage management in accordance with embodiments described herein;

DETAILED DESCRIPTION

Figure 1:
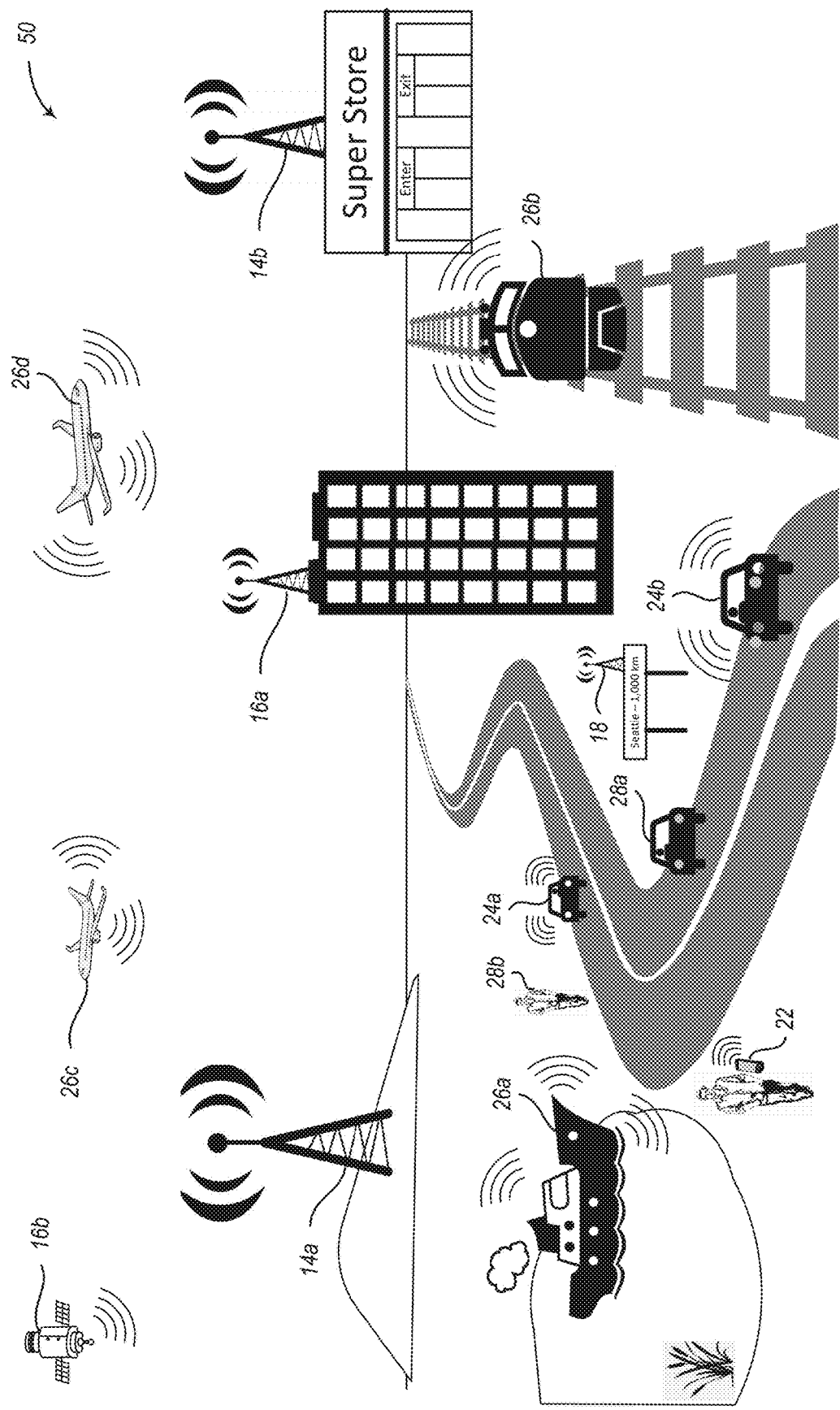
FIG. 1 illustrates a context diagram of an environment for utilizing sensor coverage management in accordance with embodiments described herein.

The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks, have not been shown or described in order to avoid unnecessarily obscuring descriptions of the embodiments. Additionally, the various embodiments may be methods, systems, media, or devices. Accordingly, the various embodiments may be entirely hardware embodiments, entirely software embodiments, or embodiments combining software and hardware aspects.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise. In addition, throughout the specification, the meaning of "a," "an," and "the" include singular and plural references.

As referred to herein, an "object" is a physical thing or item. Examples of objects include, but are not limited to, cars, planes, trains, boats, people, buildings, or other mobile or stationary things. Objects include participant objects and non-participant objects, which can be mobile or stationary. As referred to herein, a "participant" is an object that includes a computing device that can communicate specific, predetermined types of information and data to other participant objects via line-of-sight communications. And as referred to herein, a "non-participant" is an object that does not include a computing device that can communicate the same specific, predetermined types of information and data with a participant object. As discussed in more detail herein, participants can be mobile or stationary and may include computing devices of different sizes having different computing or networking capabilities. Throughout this disclosure, the term "participant" is used interchangeably with "participant object" and "participant computing device" and other related variations, and the term "non-participant" is used interchangeably with "non-participant object" and other related variations.

As referred to herein, "line-of-sight communication" refers to wireless transmission of information from a participant to another participant without other retransmission devices. Accordingly, line-of-sight is the maximum range one participant can communicate wirelessly with another participant without significant data lose. Examples of wireless transmissions used in line-of-sight communications include Bluetooth, WiFi, ADSB, TCAS, or other protocols now known or developed in the future. In some embodiments, all communications between participants utilize a common protocol.

As referred to herein, "sensor" refers to a participant's utilization of line-of-sight communications to transmit information to another participant or to detect another participant or non-participant object. For example, the sensor may include a transmitter that transmits notification signals or other data via line-of-sight communications to another participant. Notification signals are radio signals that are broadcast or directionally transmitted from a participant to send information to other participants that are within line-of-sight of the transmitting participant. As one example, notification signals may include the participant's identification information, geolocation, kinematic information, throughput capabilities, frequency capabilities, and other information regarding the participant. The sensor can also transmit data signals to other participants. Data signals are radio signals that are broadcast or directionally transmitted from a participant to another participant or computing device to send or forward messages or data packets between participants and computing devices that are in line-of-sight communication with the transmitting participant. The sensor may also include a receiver that receives echo signals of the transmitted notification signals. These echoed notification signals can be utilized to determine a location of an object, which is described in more detail in U.S. patent application Ser. No. 15/892,259, filed Feb. 8, 2018, which is herein incorporated by reference.

Sensors also include beam forming techniques and technology that enable the sensor to transmit data to or detect objects in a specific sensor coverage area. This specific sensor coverage area is determined based on the beamwidth of the sensor transmissions and a threshold line-of-sight distance of such transmissions. The threshold line-of-sight distance may be determined based on the distance away from the transmission where data loss exceeds a predetermined threshold amount, which may be based on the type of transmitter utilized, power utilization, antenna capabilities, frequency, etc. Sensors may beam form in two dimensions away from a participant or in three dimensions away from the participant. In this way, sensors can be configured to transmit data or detect objects in a specific coverage area next to, in front of, behind, above, or below the participant, or a combination thereof.

FIG. 1 illustrates a context diagram of an environment 50 for utilizing sensor coverage management in accordance with embodiments described herein. Environment 50 includes a plurality of mobile participants, a plurality of stationary participants, and a plurality of non-participants (e.g., object 28). As mentioned above, the participants can communicate specific types of information or data with one another, but cannot communicate the same types of information with the non-participants.

Briefly, each mobile participant employs one or more sensors to communicate with other participants or to detect objects in the vicinity of the participant. A computing device, such as one or more of the mobile participants, a stationary participant, or a server computer or system may manage which sensors on which mobile participants should be used by that participant and in what direction. In this way, participants can focus their sensors on an area that is not already covered by the sensors on other participants.

The following is a general discussion of the types of participants that may be utilized in such an environment and system. Embodiments, however, are not limited to these particular participants and combinations of participants. For example, in some embodiments, only tier 3 mobile participants (e.g., airplanes) may utilize the sensor coverage management described herein. In other embodiments, for example, a combination of mobile aerial participants and mobile ground participants may be utilized.

The plurality of mobile participants includes tier 1 mobile participants 22, tier 2 mobile participants 24, and tier 3 mobile participants 26. The three tiers of mobile participants are generally separated by the computing and networking capabilities of the computing devices associated with the mobile participant. The computing and networking capabilities may be limited or determined by the amount of power available or utilized by a mobile computing device, the amount of processing power available, or the size, type, or accuracy of the antenna utilized, etc.

For example, tier 1 mobile participants 22 typically have the smallest available power, lowest processing power, smallest bandwidth, shortest ranged antenna, lowest power output, lowest accuracy, and slowest update rate. Examples of tier 1 mobile participants 22 include, but are not limited to, mobile phones, laptop computers, tablet computers, wearable computing devices, or other smaller, low power, low transmission mobile computing or Internet-Of-Things devices. In the example illustrated in FIG. 1, there is only a single tier 1 mobile participant 22, which happens to be a mobile phone in this example. However, other numbers and types of tier 1 mobile participants 22 may also be employed.

Tier 2 mobile participants 24 typically have medium power constraints, a medium amount of processing power, medium bandwidth, medium range capabilities, medium accuracy, and medium update rate. Examples of tier 2 mobile participants 24 include, but are not limited to, automobiles, small personal boats, personal aircrafts, or other medium power, medium transmission, power regenerating mobile computing devices or objects that can support such mobile computing devices. FIG. 1 illustrates example tier 2 mobile participants 24 as including automobiles 24a and 24b. However, other numbers and types of tier 2 mobile participants 24 may also be employed.

Tier 3 mobile participants 26 typically have the largest available power, highest processing power, highest bandwidth, longest transmit and receive capabilities, highest accuracy, and fastest update rate among mobile participant computing devices. Example tier 3 mobile participants 26 include, but are not limited to, commercial airline planes, semi-trucks, cargo ships, trains, or other objects that can support larger, high power, high transmission mobile computing devices or objects that can support such mobile computing devices. FIG. 1 illustrates example tier 3 mobile participants 26 as including boat 26a, train 26b, and airplanes 26c and 26d. However, other numbers and types of tier 3 mobile participants 26 may also be employed.

Various embodiments described herein refer to mobile aerial participants or mobile ground participants. Mobile aerial participants and mobile ground participants are mobile participants. Thus, mobile aerial participants and mobile ground participants may likewise be separated into the three-tiers of participant capabilities.

For example, tier 1 mobile aerial participants may include personal computing devices that are onboard an airplane, such as user devices; tier 2 mobile aerial participants may include general aviation aircraft; and tier 3 mobile aerial participants may include cargo aircraft and commercial aircraft. Tier 1 mobile ground participants may include personal computing devices that are on a person walking down the street or on a car or in a boat; tier 2 mobile ground participants may include automobiles or recreational watercraft; and tier 3 mobile ground participants may include semi-trucks and cargo ships.

In some embodiments, one or more of these tiers may be further separated by capabilities or expected utilization. For example, tier 3 mobile aerial participants may include tier 3A mobile aerial participants that include cargo aircraft and tier 3B mobile aerial participants that include commercial aircraft. One situation where this distinction may occur is where a commercial aircraft is handling a lot of data requests from user devices onboard the aircraft (e.g., tier 1 mobile aerial participants), which may impact that aircraft's throughput for forwarding communications between other participants. Conversely, a cargo aircraft is typically not handling a lot of data request from user devices onboard the aircraft, but is instead primarily being used to forward communications between other participants.

Although some embodiments may be described herein with respect to mobile aerial participants, embodiments are not so limited. Those same embodiments may instead utilize mobile ground participants or a combination of mobile ground participants and mobile aerial participants, unless the context clearly indicates otherwise.

The plurality of stationary participants includes ground entry points 14, remote entry points 16, and access nodes 18. In some embodiments, stationary participants may be referred to as ground participants. Similar to the three tiers of mobile participants, the ground entry points 14, remote entry points 16, and access nodes 18 are generally separated by computing and networking capabilities, and footprint size in some embodiments.

For example, ground entry points 14 typically have the largest available power, highest processing power, highest bandwidth, and longest range antenna capabilities. Example locations of ground entry points 14 include, but are not limited to, cellular towers, airports, large retail or superstores, or other locations that can support large sized, high power, high transmission stationary computing devices. FIG. 1A illustrates example ground entry points 14 as including tower antenna 14a and superstore 14b. However, other numbers and types of ground entry points 14 may also be employed.

Remote entry points 16 typically have medium power constraints, a medium amount of processing power, medium bandwidth, and medium range capabilities. Example locations of remote entry points 16 include, but are not limited to, restaurants and coffee shops, airfields and train stations, satellites, or other locations that can support medium sized, medium power, medium transmission stationary computing devices. FIG. 1A illustrates example remote entry points 16 as including store antenna 16a and satellite 16b. However, other numbers and types of remote entry points 16 may also be employed.

Access nodes 18 typically have the smallest available power, lowest processing power, lowest bandwidth, and shortest range antenna capabilities of the stationary participants. Example locations of access nodes 18 include, but are not limited to, road intersections, train crossings, road signs, mile markers, crosswalks, or other locations that can support smaller, low power, low transmission stationary computing devices. In the example illustrated in FIG. 1A, there is only a single access node 18, which happens to be a road sign in this example. However, other numbers and types of access nodes 18 may also be employed.

As mentioned herein mobile and stationary participants can communicate with one another to pass information from one participant to another.

Figure 2:
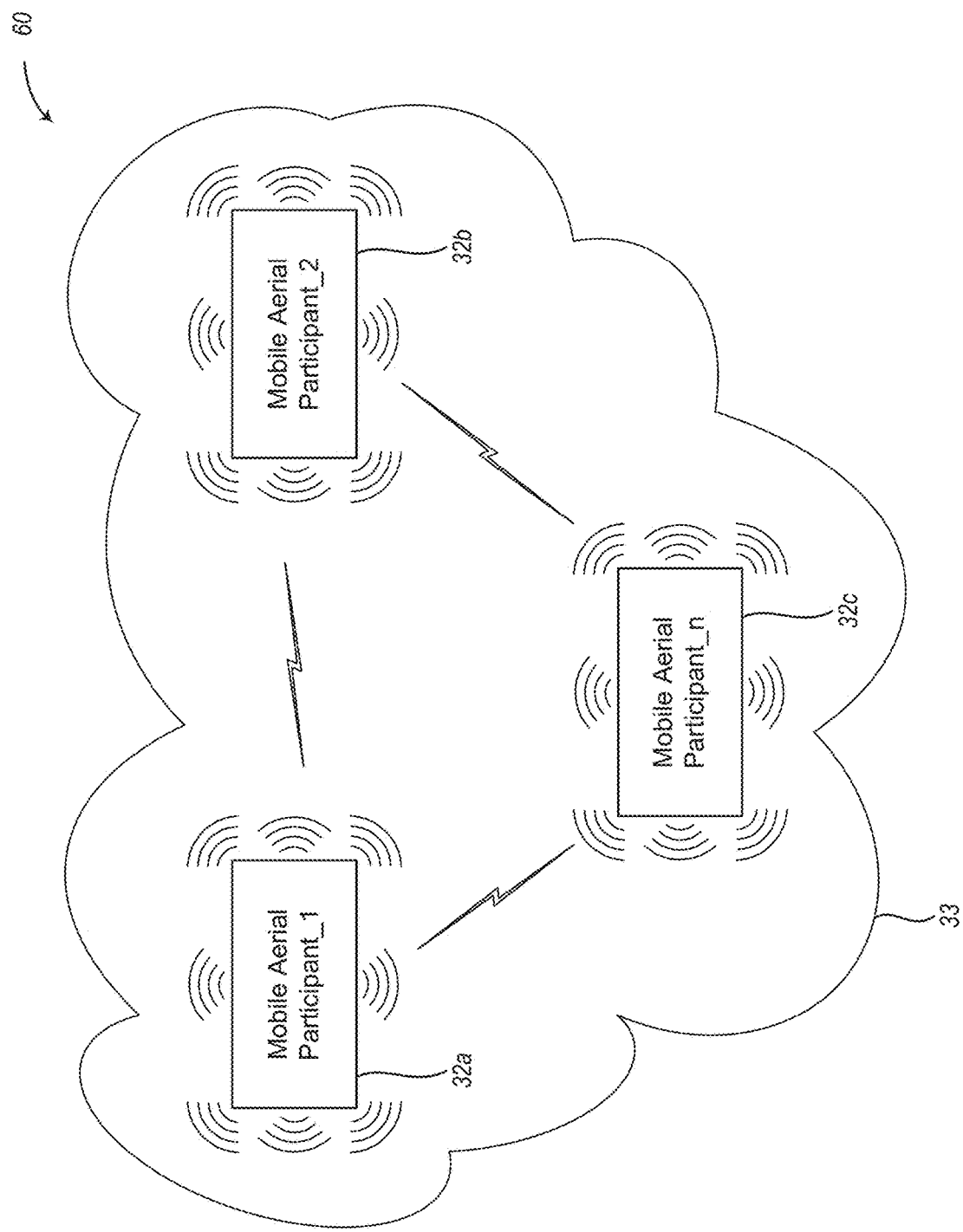
FIG. 2 illustrates a block diagram of a communication network between participants in accordance with embodiments described herein.

FIG. 2 illustrates a block diagram of a communication network between participants in accordance with embodiments described herein. FIG. 2 illustrates an example 60 of a communications network 33 between a plurality of mobile aerial participants 32a-32c. Collectively, the mobile aerial participants 32a-32c may be referred to as the network. Although FIG. 2 only illustrates three mobile aerial participants as creating network 33, embodiments are not so limited and one or a plurality of mobile aerial participants may be employed. Similarly, the network 33 may be established from other types of mobile participants, including various combinations of tier 1 mobile participants, tier 2 mobile participants, or tier 3 mobile participants, which perform many of the same functions as the mobile aerial participants.

Each mobile aerial participant 32a-32c transmits radio frequency signals to be received by other mobile aerial participants 32 that are within line-of-sight of the sending mobile aerial participant 32. These signals include, but are not limited to (1) data signals that transmit messages or data to another participant and (2) notification signals that provide personalized information regarding the sending mobile participant. In some embodiments, the notification signals are referred to as self-reporting messages or self-reporting signals. The notification signals can include one or both of notification signals for networking and routing among participants and notification signals for safety and de-confliction of possible threats.

The notification signals serve three primary simultaneous purposes: (1) to notify other participants of the sending participant's identity, position, and kinematic information; (2) to detect and track non-participant objects; and (3) to establish routing and network efficiencies (i.e., to create the participant table identifying where each participant is and with who they are in line-of-sight communication). In various embodiments, the notification signals provide individualized information regarding the sending mobile aerial participant 32 so that other mobile aerial participants 32 know that they are within line-of-sight communication of the sending mobile aerial participant 32 within network 33. These notification signals may be referred to as self-reporting signals, since the mobile aerial participant 32 is independently reporting its position and kinematic information to any other mobile aerial participants 32 that are within line-of-sight of the transmitting mobile aerial participant 32 without being prompted or requested by another mobile (or stationary) participant. The mobile aerial participants 32 utilize the notification signals to generate a participant table that is utilized to transmit data signals between the mobile aerial participants 32.

In various embodiments, the information in the notification signal includes the mobile aerial participant's 32 identification information, geolocation, kinematic information, throughput capabilities, frequency capabilities, number and capability of sensors, and other information. In various embodiments, the notification signals also include transmission time information that allows for Time Distance of Arrival (TDOA) and Time of Flight (TOF) or Round Trip Timing (RTT) calculations.

The geolocation of the mobile aerial participant 32 may be determined via traditional methods like GPS sensors or modules, cell tower or stationary participant signal triangulation, or via notification messages from other devices or participants that know or estimate the position or location of the mobile aerial participant 32. This can be accomplished with extreme accuracy and minimal latency when notification messages are echoed and supported by stationary participants. The geolocation may also be referred to as the position or location of the mobile aerial participant 32.

The kinematic information may be obtained by monitoring the mobile aerial participant's 32 position and identifying changes over time, utilizing various sensors to calculate or determine the kinematic information, or obtaining it from another system.

The frequency capabilities of the mobile aerial participant 32 may be predetermined based on the type of hardware utilized by the mobile aerial participant 32. For example, the hardware of the mobile aerial participant 32 may be designed to utilize ACARS, IEEE 802.11 standards, or some other wireless transmission frequencies or standards, which defines the frequency capabilities of the mobile aerial participant 32. In other embodiments, the frequency capabilities may be predetermined based on government regulations regarding available frequencies. In yet other embodiments, the frequency capabilities may be defined by a user or administrator.

The throughput may be predetermined based on the type of hardware utilized by the mobile aerial participant 32 or on the current processing capacity or network traffic of the mobile aerial participant 32 or a number of other factors. For example, if the mobile aerial participant 32 is a Boeing 737-700 then it may have more throughput capabilities than a Boeing 777-200ER because the Boeing 737-700 may have less passengers and thus may be supporting fewer data requests from user device onboard the airplane, which can allow for more possessing power to be directed towards forwarding communications between other participants.

The number and capability of sensors may identify the type of sensors, where their particular antennas are attached to the participant, the range/transmission capabilities of the sensors, their beamwidth characteristics, or other information regarding the sensors on the corresponding participant.

Notification signals are transmitted via directional broadcast beams. In various embodiments, directional notification signals may be transmitted in a sequential or non-sequential 360-degree pattern, so that the notification signal is transmitting in all directions surrounding the participant. In some embodiments, where there is little to no sensor overlap, the notification signals may be transmitted using directional or non-directional broadcast signals. In general, the use of the term "broadcast" herein refers to the transmission of a signal by a sending participant without being requested by another participant and does not have a specific participant as a destination.

Use of directional transmissions can reduce the amount of power needed to transmit the notification signal or other communication to another participant, while also providing additional versatility in providing additional sensor coverage by at least one sensor on at least one participant in an area. Moreover, the use of directional transmissions enables the sending participant to use just enough power to ensure it gets to its intended target. Additionally, directional transmissions can reduce interference between transmissions in a congested space as well as make transmissions more secure.

The notification signal may be broadcast periodically, at predetermined times, dynamically selected based on number and proximity of other mobile aerial participants, or at a given dynamically changing update rate. In some embodiments, the rate at which the mobile aerial participant 32 transmits its notification signal may change based on a combination of the distance, closure velocity, and closing angles between the sending mobile aerial participant 32 and other mobile aerial participants 32 within line-of-sight of the sending mobile aerial participant 32.

The mobile aerial participants 32a-32c transmit notification signals to inform other mobile aerial participants 32 of their position and movement. For example, mobile aerial participant 32a transmits notification signals with information identifying itself and its respective geolocation and kinematic information without regard to the presence or location of mobile aerial participants 32b or 32c. If mobile aerial participant 32c is within line-of-sight of mobile aerial participant 32a, mobile aerial participant 32c receives the transmitted notification signals from mobile aerial participant 32a and utilizes the information in the notification signals, and its own location and kinematic information, to identify the position and movement of mobile aerial participant 32a relative to itself.

The mobile aerial participants 32 can utilize the notification signals to track other participants and non-participants (e.g., by using echo signals of the notification signals to locate objects) and to create and update the participant table to identify which participants are in network 33, their location, their capabilities, and who they are in line-of-sight communication. The various communications between the mobile aerial participants 32a-32c creates a communication network 33 among each other that enable them to communicate with one another without the use of another communication backbone, such as a cellular tower network.

The data signals transmitted by one participant to another participant may be transmitted via directional transmission beams or non-directional transmission signals. In various embodiments, the sending mobile aerial participant 32 utilizes a participant table to determine a location of the recipient participant. The sending mobile aerial participant 32 can directionally focus the transmitted data signals towards the recipient participant based on the position of the sending participant and the position of the recipient participant. The use of directional transmissions can reduce power consumption and increase the range in which transmission can be received, while also reducing interference between transmissions in a congested space.

Although not illustrated, other mobile participants and stationary participants may also perform similar actions as described above to identify and track mobile participants that are in line-of-sight to support management of the participant table and to communicate data or information amongst themselves to increase accuracy and efficiency of each participant.

Figure 3:
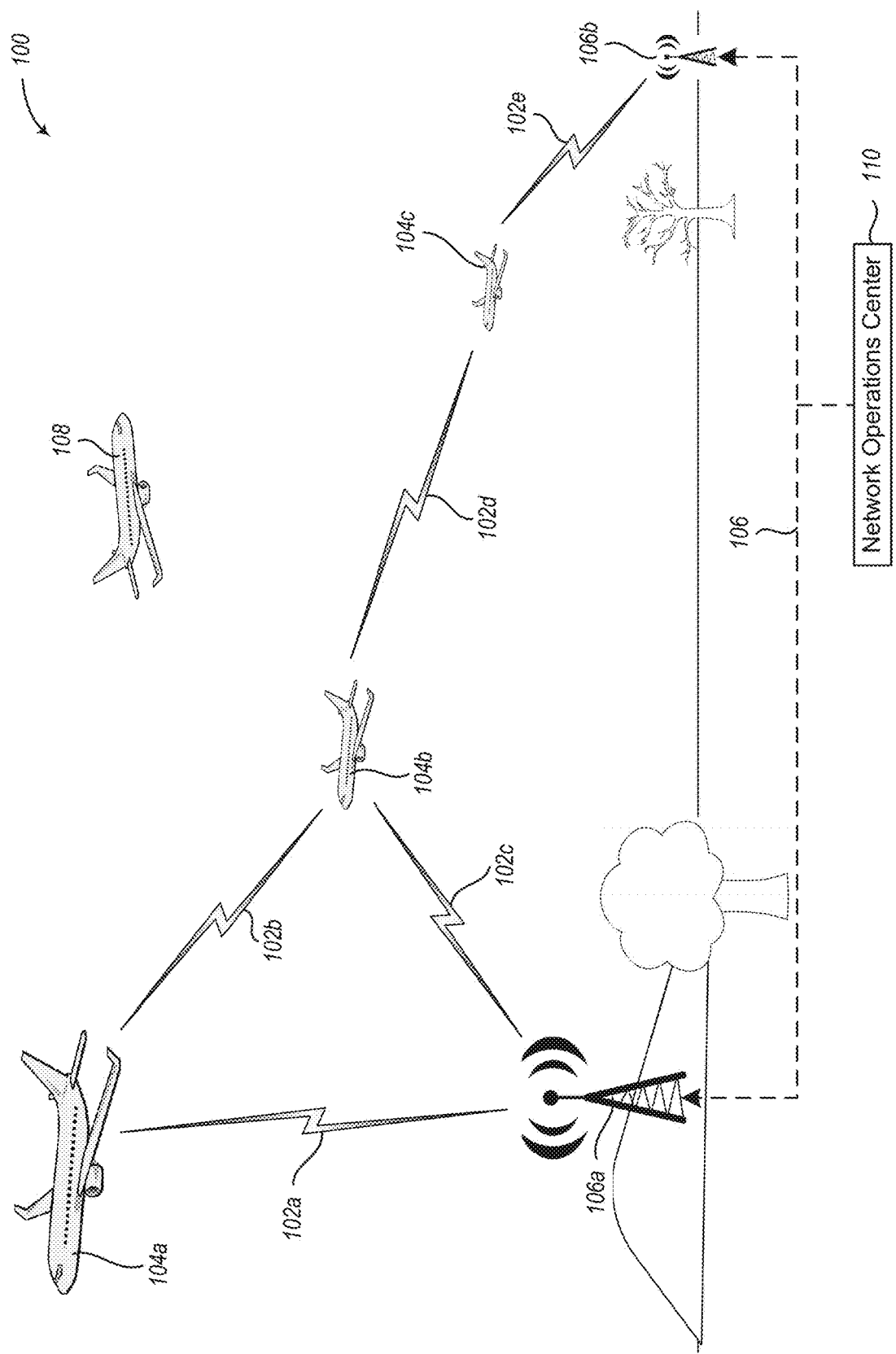
FIG. 3 illustrates a context diagram illustrating a use-case example of employing sensor coverage management to transmit data in accordance with embodiments described herein.

FIG. 3 illustrates a context diagram illustrating a use-case example of employing sensor coverage management to transmit data in accordance with embodiments described herein. Example 100 illustrates a plurality of mobile aerial participants 104a-104c. Each mobile aerial participant 104a-104c utilizes one or more sensors to transmit notification signals and data signals to other participants, such as mobile aerial participants 104a-104c, or to stationary participants 106a-106b, via line-of-sight communications 102a-102e. Similarly, each mobile aerial participant 104a-104c also tracks the position of the other mobile aerial participant 104a-104c and any non-participants 108.

Each mobile aerial participant 104a-104c, one or more stationary participants 106a-106b, or a network operations center 110 (i.e., one or more server computing systems) maintains a network database with information about each participant. For example, the network database may store information for each participant, such as a unique identifier that has been registered within the network, specific type aircraft, nationality, owner, transmit/receive capabilities (e.g., spectrum, polarity, type and location of antennas or sensors), etc. This information can be transmitted, along with kinematic or other data, in notification signals or other types of transmission signals, to paint a three-dimensional picture of sensor coverage within the network. As used herein, a three-dimensional picture of sensor coverage refers to the general physical space in which at least one sensor on at least one participant can detect an object that is located with the physical space. A total sensor coverage area would indicate that at least one sensor on at least one participant can detect an object that is located within a predefined space or geographical area (e.g., from the ground to 40,000 feet over the continental United States). A partial sensor coverage area would indicate that there are areas within the predefined space or geographical area where no participant sensor would detect an object. Partial sensor coverage can occur if participants are too far from one another for their sensor coverage areas to touch or overlap, technical restraints (e.g., sensors that have a limited beamwidth or cannot beamform to an area not already covered by another sensor), etc.

The sensor coverage area of one or more of the mobile aerial participants 104a-104c can be managed locally (i.e., between the mobile aerial participants that are within line-of-sight of one another), by the stationary participants 106a-106b, by a network operations center 110, or a combination thereof. The participant that maintains the sensor coverage area may be static or dynamic and may be set or changed based on application. For commercial airlines, for example, where data throughput is a high priority, the stationary participants 106a-106b or the network operations center 110 may manage sensor coverage due to the desire to preserve bandwidth among the mobile aerial participants 104a-104c. In a government or military application, on the other hand, the mobile aerial participants 104a-104c may manage sensor coverage within line-of-sight participants due to the desire for decreased latency—even though it may reduce bandwidth.

Each mobile aerial participant 104a-104c has known antenna locations and maximum coverage areas based on the system configuration that will be available in the participant database. The known antenna locations and their maximum coverage area may also be referred to as the sensor location and the maximum coverage area for that sensor. As sensor coverages overlap it brings opportunity to both integrate and deconflict participants and non-participants. Deconflict refers to the detection and tracking of objects (participant and non-participant) such that actions can be performed to avoid a collision or threat of collision.

Each mobile aerial participant 104a-104c, or an area surrounding each mobile aerial participant 104a-104c, or group of mobile aerial participants 104a-140c, or a total physical area/space includes a threshold coverage area. As one example of such threshold coverage area, each mobile aerial participant 104a-104c may have an individual threshold coverage area that targets a 15 degree wide, 10 kilometer area off the front of the mobile aerial participant 104a-104c. As another example, a particular air space may have a total threshold coverage area that is targeted to be fully covered by sensors in a 20 kilometer radius from 10,000 feet to 40,000 feet. In various embodiments, there may be an overall system or physical space coverage threshold as well as individual thresholds for each participant.

The system that is managing the coverage area—whether it is one or more of the mobile aerial participants 104a-104c, one or more stationary participants 106a-106b, or the network operations center 110—determines the current individual sensor coverage area of the participants within the desired coverage area based on the location of the participants, the number and location of the sensors on the participants, the capabilities of the participants, the movement of the participants, etc. The managing system aggregates the individual coverage areas and compares them to one another to determine if the total sensor volume coverage threshold has been met, as well as each individual participant and non-participant threshold. In some embodiments, the total volume coverage or the individual participant or non-participant thresholds may be set by a particular customer, organization, or governing body (e.g., FAA, DoD, Airfield, Distribution Center, etc.).

Once volume coverage thresholds (individual or system-wide) and tracking thresholds are met, the system determines if there are individual sensor coverage areas that unnecessarily overlap one another, such as based on some overlap threshold amount or percentage. If so, the system determines which sensor is the least beneficial (e.g., is fully overlapped by one or more other sensors) to the coverage area and instructs its corresponding participant to turnoff or adjust that particular sensor. For example, if sensor_A on mobile aerial participant 104b covers a same area as sensor_B on mobile aerial participant 104c for the area between the two participants, then mobile aerial participant 104b can stop using sensor_A to detect objects or it can change the beamform of the sensor to be at a different horizontal area or elevation or ignore the area between the two participants. In this way, participant 104b can save throughput by not having to scan the area between participant 104b and 104c, which can allow the participant 104b to use sensor_A to scan another area where the coverage area has not been met or to focus additional scans on tracking non-participant 108. As a result, the aggregate of all sensors of all participants in the network can be maximized for efficiency or the network coverage can be modified to maximize coverage area.

In some other embodiments, other characteristics of the participants or their sensors may be utilized to determine which sensors to modify to reduce or remove the overlapped coverage area. In at least one such embodiment, the sensor/system timeline availability of one or more sensors, or of a participant, associated with the overlapped coverage area may be evaluated to determine which sensors to adjust. The sensor/system timeline availability may be referred to as the amount of computer processing associated with a given task being performed by a sensor or computing system on the participant. For example, sensor timeline availability for a given sensor may be an amount of computer processing power utilized to process sensor data for the current refresh rate of the sensor. For example, a full timeline may include more frequent scans (e.g., a higher refresh rate) that utilize more processing power to process and analyze the scanning data. Conversely, an empty timeline may include less frequent scans (e.g., a lower refresh rate) that utilize less processing power. The sensor/system timeline availability may also be employed at the participant level, such as how much processing power is being utilized by the participant to perform actions (e.g., transmitting information to other participants, tracking other participants or objects, performing self diagnostic procedures, etc.).

In various embodiments, participants or their sensors can be load managed or balanced to determine which sensors to adjust to reduce the overlapping coverage area. For the following examples, assume the coverage area of sensor_A on participant_A overlaps the coverage area of sensor_B on participant_B. In some embodiments, if sensor_A has very little available timeline (e.g., sensor_A has a higher refresh rate and is utilizing high amounts of processing power) compared to sensor_B (e.g., sensor_B has a lower refresh rate and is utilizing low amounts of processing power), then the coverage area of sensor_A may be reduced to remove the overlap without adjusting the coverage area of sensor_B. In other embodiments, if both sensors are operating with little available timeline, then the reduction in the overlapping coverage area may be split between both sensors, such that the coverage area of both sensors is adjusted to remove the overlapped coverage area. This adjustment may be equal or it may proportional to the sensor/system available timeline. For example, if sensor_A is utilizing 20% more processing power than sensor_B, then the coverage area of sensor_A may be reduced more than the coverage area of sensor_B.

In yet another embodiment, the coverage area of the overlapping sensors may be reduced and the coverage area of another non-overlapping sensor may be increased. For example, consider the example above with sensor_A overlapping sensor_B, but where their overlap is only 20%. If both sensors are utilizing high amounts of processing power, but sensor_C is utilizing very little processing power, then the coverage areas of sensor_A and sensor_B may be reduced to create a non-covered area, which can then be covered by sensor_C. Therefore, the sensor/system timelines of sensors or participants can be load managed and balanced against each other to reduce or remove the overlapping coverage area, while also reducing the overall amount of processing being performed by the participants.

In various embodiments, one or more different thresholds may be utilized to determine which sensors to adjust to remove or reduce the overlapping coverage area. examples of such thresholds may include, but are not limited to, processing power, total processing capacity, memory usage or availability, sensor capabilities, current sensor coverage areas, travel direction, travel speed, etc.

As described herein, the aggregated coverage area of multiple sensors may also result in missing coverage areas between the volume coverage thresholds (individual or system-wide) and the tracking thresholds. In various embodiments, system can identify those missing coverage areas and modify sensor coverage areas (on the participant or by instructing other participants) to remove or reduce the missing coverage areas. In various embodiments, the participants or their sensors can be load managed or balanced to determine which sensors to adjust to reduce the missing coverage area, similar to what is described above for removing an overlapping coverage area. For example, a sensor/system that has a lot of available timeline may be adjusted to cover at least a portion of the missing coverage area, whereas a sensor that has very little available timeline may not be adjusted (or may be adjusted only a small amount compared to the other sensor).

In various embodiments, the system that is managing the coverage area may send periodic updates to the participants indicating the particular coverage for each sensor on that corresponding participant. In other embodiments, the system may notify the participants of the location of new or moved participants or non-participants in a target coverage area. In other embodiments, the system may provide updates only to those participants that are to deconflict an object. In at least one embodiment, a participant can override their sensor coverage provided by the system and focus their sensors on tracking for collision avoidance on particular objects that pose a serious threat to the participant. Overall, sensor management at the network level allows participants to modify their coverage to meet mission needs based on information provided by the system that is aggregating sensor coverage from multiple sensors and multiple participants.

In some embodiments, participants communicate their sensor coverage to other participants based on safety, threat avoidance, or overall network coverage (e.g., pre-determined area surveillance), which may be based on a priority schema. For example, participants can manage their sensor/system timeline availability such that its own system safety has the highest priority. Once the participant determines that it is safe (e.g., by satisfying one or more safety thresholds that may indicate that the participant is operating at a satisfactory level and is not currently in danger of crashing or having other safety issues), then the participant can utilize sensor/system timeline availability to identify potential threats (e.g., objects that may eventually cross paths with the participant) to the participant or to other participants. Once the participant determines that it has identified and is tracking possibly threatening objects, then the participant can utilize sensor/system timeline availability to support the overall network coverage (e.g., surveillance volume).

In various embodiments, participants may share their own safety and threat thresholds, their individual system or sensor capabilities, their current operating capacity (e.g., is the participant solely focused on safety or is it using some of its processing power for network coverage), etc. with other participants. Participants can utilize this shared information from other participants, along with their own priority schema and sensor/system timeline availability, to determine if and how it can provide support for the total network coverage. In various embodiments, if a participant is notified that there is a missing coverage area in which the participant can provide coverage (or that participant itself identifies the missing coverage area), that participant determines if has sufficient sensor/system timeline availability given its current priority thresholds.

For example, if the participant is utilizing half of its available timeline to process an extremely high safety issue, then that participant may ignore the missing coverage area and not increase its sensor coverage area to reduce the missing coverage area. In at least one embodiment, the participant may notify other participants that it is unable to help reduce the missing coverage area. The other participants can then determine if they can help reduce the missing coverage area.

As another example, if a participant is utilizing most of its available timeline to process an extremely high safety issue, then that participant may notify other participants that it is decreasing its sensor coverage area. The participant may first decrease sensor coverage where there is an overlapping coverage area with another participant; otherwise, the participant may decrease a low-priority coverage area for the participant. This reduction of sensor coverage may result in a missing coverage area for the overall network coverage. By decreasing its sensor coverage area, the participant allows itself to continue to have sufficient processing power to deal with the safety issue. Once the safety issue is resolved, the participant can again provide support for the overall network coverage. In at least one embodiment, the participant may notify other participants that it is reducing its coverage area. The other participants can then determine how the reduced coverage impacts the overall network coverage.

In various embodiments, the use of the priority schema may be employed in conjunction or in combination with the load management and balancing described above. The use of priorities, sharing of information, and load management enables participants to determine which participants and which sensors may be utilized to provide individual (or localized) safety and threat coverage, while also contributing to the overall network coverage. In this way, participants work individually and together to keep all participants safe, maintain thresholds on all threats, and provide network-wide surveillance volume.

In various embodiments, the thresholds described herein (e.g., safety or threat thresholds, individual coverage thresholds, network coverage thresholds or surveillance volume, etc.) can be set during pre-planning, set or adjusted in real-time by operators, or set or adjusted in real-time by the system based learned information. The pre-planning setup of thresholds may be based on the goals or parameters of the participants. For example, if a goal of the participants is to identify and track unknown participants in a given geographic area, then total or near-total network coverage in the given geographic area may be selected. Conversely, if the goal of the participants is to not crash, then the overall network coverage may very limited. The real-time setup or adjustment of thresholds may be employed by an operator based on changes in the goals or parameters or other current conditions. For example, if an operator determines that there are a lot of non-participant objects in an area, then the operator may increase its threat avoidance threshold. The setup or adjusted of thresholds may also be employed by the system based learned information. For example, artificial intelligence or machine learning may be employed to determine how components of the participant are working or reacting to the current conditions (e.g., the system may detect that the participant is taking 20% longer to slow down and stop), which can allow for the system to automatically adjust one or more thresholds to account of the changed conditions. The above described examples are for illustrative purposes and should not be construed as exhaustive or limiting.

As discussed above, each participant can employ a priority schema to prioritize their sensor/system timeline usage and availability to ensure the participant's safety thresholds are met followed by the participant's threat thresholds and finally supporting overall network coverage. Such a priority schema may also be employed at a network level. In various embodiments, the information communicated between participants (e.g., safety and threat thresholds, individual system or sensor capabilities, participant current operating capacity, participant location information, etc.) can be utilized by participants to further aggregate and support network-level safety and threat thresholds. For example, participants can utilize or aggregate sensor coverages (its sensor coverage, other participant sensor coverages, or a combination thereof); utilize or modify sensor refresh rates; select or modify spectrum allocation; or aggregate, monitor, modify, or utilize other information to meet network-level safety and threat thresholds.

As one non-limiting example, if participant_A is experiencing a safety issue that it cannot resolve itself and participant_B is in proximity to participant_A, then participant_B may dedicate sensor/system timeline availability to help resolve the safety issue to participant_A. However, participant_B may only provide support if that support does not compromise its individual safety or threat thresholds. This extra support from participant_B may include increased refresh rate of its sensors to monitor participant_A or some other object causing the safety issue, increase data transmissions or throughput to inform other participants of the safety issue, or other types of actions. After participant_B has supported participant_A (e.g., the safety issue to participant_A has been resolved or participant_B has traveled away from participant_A and can no longer help), participant_B can increase its support to other, possibly lower priority, tasks (e.g., supporting the overall network volume coverage.

In various embodiments, the individual priority schemas and the network priority schema may be integrated. For example, in some embodiments, the individual participant safety has the highest priority followed by other participant safety followed by individual participant threat tracking followed by other participant threat tracking followed by overall network coverage. In other embodiments, the individual participant safety has the highest priority followed by individual participant threat tracking followed by other participant safety followed by other participant threat tracking followed by overall network coverage. The particular priority order between the individual priority schema and the network priority schema may be set by an administrator, based on the goals and purpose of the participants, based on the utilization of the participants, based on the type of participants, adjusted based on current operating conditions of the participants throughout the network, or other selected factors.

By having participants implement individual priority schemas, while supporting network-level priority schemas, participants are better able to manage their sensor/system timeline availability, while also supporting other participants and overall network health.

Moreover, each separate category of thresholds may also include an internal priority schema with one or more levels of priority. For example, with regards to the safety thresholds for a participant, the participant may prioritize a lack of fuel higher than a reduction in cabin pressure. Likewise, for the threat thresholds, the participant may prioritize an object on a projected collision course with the participant at a higher priority than an object close to but moving away from the participant. The number and order of priorities may be pre-determined based on the type of safety issue or threat, pre-set by an administrator, modified by an operator based on current conditions, etc.

This type of multiple internal priority levels can also be applied to the overall network volume coverage threshold. For example, assume the participants are mobile aerial participants. Some airspace may be given a higher priority than other airspace. The particular priorities may be determined based on location, goals or purpose of the participants, time of day, or other constraints or conditions, and they may be defined by an administrator, set by an operator, selected based on learned information from previously collected data, etc.

For example, assume a first government agency is focused on general aviation monitoring and safety. This first government agency may prioritize the airspace based on air routes that have a traffic volume or density above a selected threshold. In this example, the altitude and locations associated with defined air routes may have a higher priority than non-route altitudes and locations. This type of prioritization allows for participants to focus or provide additional coverage for the overall network coverage in those higher priority areas.

As another example, a second government agency may be focused on monitoring the movement or capabilities of an enemy. This second government agency may prioritize the airspace based on the enemy's geographic area. In this way, the airspace above the enemy's location is given a higher priority than the surrounding areas. Moreover, if the second government agency has knowledge of the enemy using a particular type of aircraft, then the priority of the airspace over the enemy's location may be further prioritized based on the profile and characteristics of that aircraft. In this example, the altitude associated with the aircraft's capabilities may be assigned a higher priority than other altitudes.

To support higher priority areas, participants may increase the amount of overlapping coverage, increase sensor refresh rates, modify other sensor parameters to provide improved monitoring accuracy, or even prioritize overall network coverage over low priority individual threat thresholds. Conversely, in lower priority areas, participants may tolerate missing coverage areas, decrease sensor refresh rates, etc.

Figure 4A:
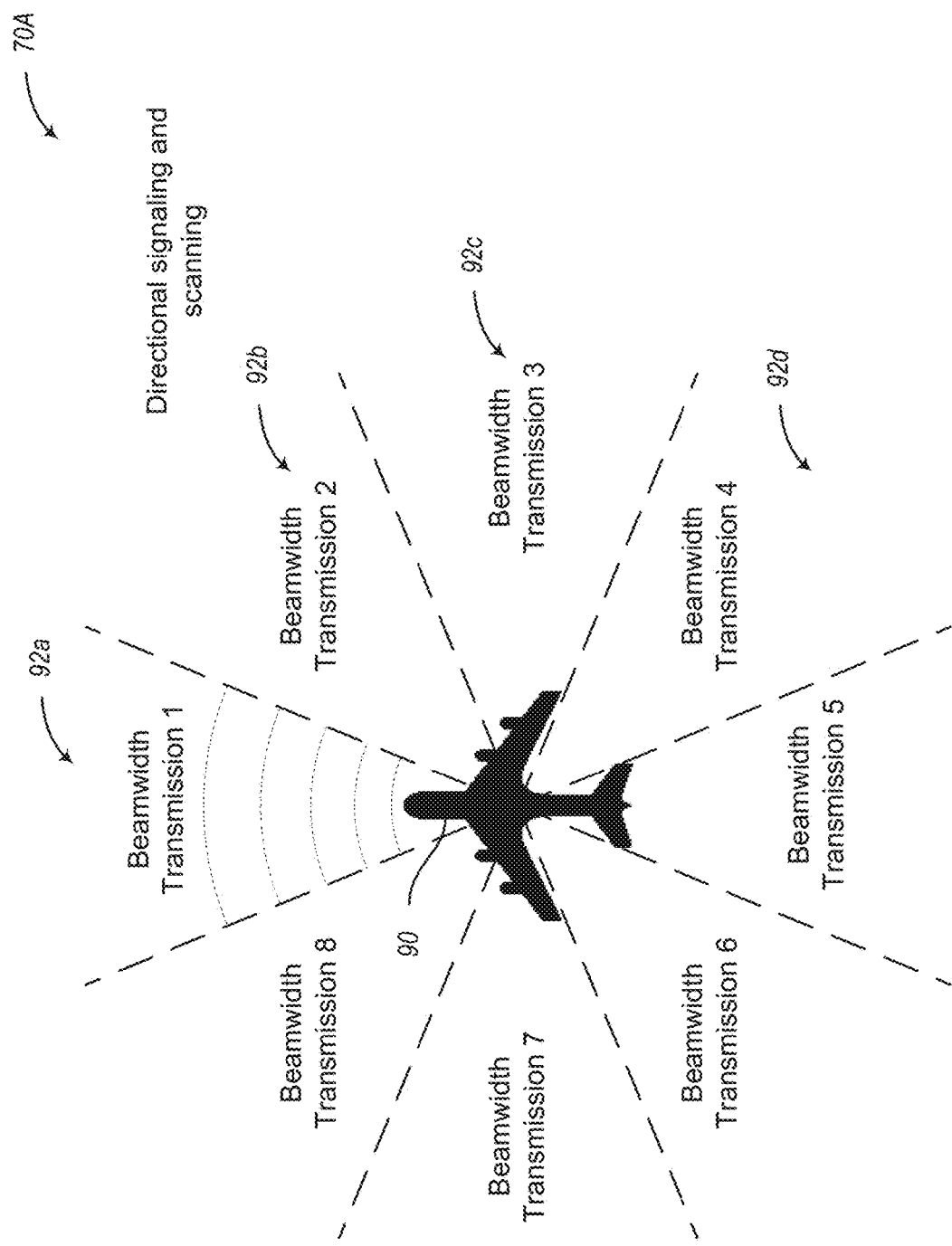

FIGS. 4A-4B illustrate context diagrams of using directional signaling and scanning to provide directional communication between participants in accordance with embodiments described herein. FIG. 4A illustrates an example 70A of first participant 90, such as an airplane, transmitting directional notification signals 92a-92d. As shown, each notification signal 92 is transmitted away from the first participant 90 at a particular angle with a particular beamwidth. In various embodiments, the first participant 90 waits a predetermined amount of time before transmitting the next notification signal 92 at the next angle. In other embodiments, the first participant 90 may continuously transmit the next notification signal at the next angle and utilize phased, frequency, and polarity shifts to allow for simultaneous transmission and reception of notification signals. The beamwidths of the notification signals 92 may not overlap, e.g., as illustrated in FIG. 4A, or they may partially overlap one another.

In the illustrated example in FIG. 4A, the first participant 90 transmits eight notification signals with 45 degree beamwidth to cover 360 degrees around the first participant 90. Although FIG. 4A illustrates the notification signals as two-dimensional transmissions, embodiments are not so limited, and the notification signals may be transmitted as three dimensional signals, such as a cone shape. In some embodiments, the first participant 90 may transmit a first set of notification signals at a first elevation, e.g., with a center of the transmission on a horizontal axis from the first participant, and a second set of notification signals at a second elevation, e.g., with a center of the transmission at a 30 degree angle towards the ground. The first participant 90 may continue with additional sets of notification signals as different vertical or elevational angles to create a three-dimensional coverage area.

In various embodiments, the first participant 90 transmits the notification signals 92 in a sequential order. For example, notification signal 92a is transmitted first, followed by notification signal 92b, which is followed by notification signal 92c, and so on. A complete transmission cycle occurs when all eight notification signals 92 have been transmitted. A complete transmission cycle is used to notify other participants within line-of-sight of the first participant 90 of the first participant's 90 location and kinematic information.

Figure 5:
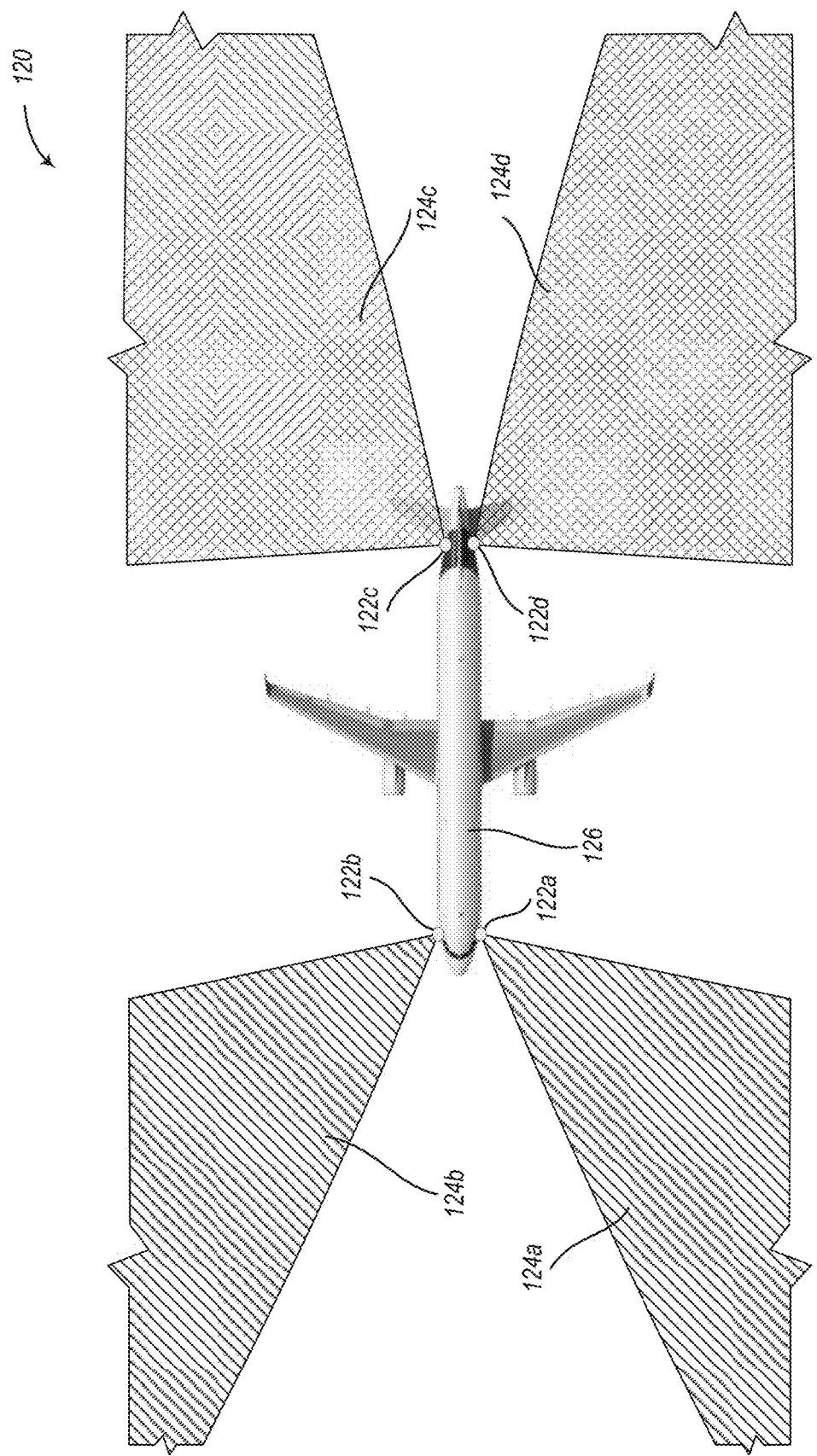
FIG. 5 illustrates a context diagram illustrating a use-case example of directional sensors being employed by a participant in accordance with embodiments described herein.

Although FIG. 4A illustrates eight notification signals being used for a complete transmission cycle, other numbers of notification signals at other beamwidths may also be utilized. Moreover, the first participant 90 may include one or a plurality of sensors that each performs such directional notification signals, which is illustrated in FIG. 5. In at least one such embodiment, each sensor may include a complete transmission cycle that is 360 degrees, 90 degrees, or some other total coverage area. Moreover, a complete transmission cycle may include one or more different planes or levels in a 3-dimensional area around the first participant 90. For example, a given sensor may have a 90 degree horizontal beamwidth area to cover, but also include a positive 45 degrees and negative 45 degrees vertically with respect to the horizon of the first participant 90—although other coverage areas may be employed.

In various embodiments, a complete transmission cycle is performed at a given update rate, which may be predetermined or may dynamically change. For example, in some embodiments, the update rate may be faster when there are more participants or non-participant objects near the first participant 90, compared to when there are few or no objects near the first participant 90. In other embodiments, the update rate may be faster when the first participant 90 is moving at a higher speed compared to when the first participant 90 is moving at a slower speed.

In some embodiments, the first participant 90 may also maintain individualized update rates for each participant that is in line-of-sight of the first participant 90. However, since the first participant 90 does not request the positional information from other participants, it can utilize only the received notification signals based on the update rate, while ignoring every other notification signal from the other participant. For example, if another participant is transmitting notification signals once every second, but the first participant 90 has an update rate of once every five seconds for the other participant, then it may utilize one of the five notification signals that it receives in a five second period while ignoring the rest. This individualized update rate may dynamically change based on the distance and velocity of closure between the first participant 90 and the other participant object. In this way, the first participant 90 utilizes more notification signal from the first participant 90 when the other participant and the first participant 90 are closer together or traveling towards each other such that there is a treat of potential collision, and ignores superfluous notification signals if they are far apart or traveling away from one another. In other embodiments, participant 90 can use one of its self-reported notification signals to communicate to other participants within line of sight to increase its update rate, if needed.

FIG. 4B illustrates an example 70B of a second participant 94 coming within line-of-sight of the first participant 90 while the first participant 90 is transmitting directional notification signals 92.

As shown in FIG. 4B, the notification signal 92d is transmitted away from the first participant 90. The second participant 94 receives the notification signal 92d. Based on the information in the notification signal 92, the second participant 94 updates the participant table. Likewise, the second participant 94 is also transmitting notification signals, not illustrated, that are being received by the first participant 94.

When the first participant 90 has a message or communication to transmit to the second participant 94, the first participant 90 utilizes the participant table to determine the location and movement of the second participant 94 relative to the location and movement of the first participant 90. The first participant 90 can then directionally transmit a signal, similar to the directional transmission of the notification signal 92d, to the second participant 94 with the message or communication. In general, notification signals are not directed towards a specific participant, but data transmission signals are directed towards a specific participant. In this way, the transmission power can be focused on a relatively narrow beamwidth rather than a non-directional broadcasted message, which improves power utilization and reduces the chance of interception by third parties.

Although not described in detail herein, the first participant 90 can receive an echo signal of the notification signal off the second participant 94 to determine a position of the second participant object 94. The first participant 90 can calculate the approximate distance the second participant 94 is away from the first participant 90 based on the time of flight from the transmission of the notification signal 92d to the receipt of the echo signal. This approximate distance is used to determine an approximate position 98 of the second participant 94.

Utilization of the echo signal from the notification signal can be helpful in identifying and tracking non-participants. Similarly, such independent determination of the approximate position of the second participant 94 may be utilized if a participant's equipment is malfunctioning and not transmitting notification signals or if the information in its notification signals is not accurate. Thus, this approximated position calculation can be compared to the location information in the notification signals to confirm that the information in the notification signals is accurate.

FIG. 5 illustrates a context diagram illustrating a use-case example of directional sensors being employed by a participant in accordance with embodiments described herein. Example 120 illustrates a mobile aerial participant 126 that includes four sensors 122a-122d. Each sensor 122a-122d provides an independent coverage area 124a-124c, respectively. Each sensor 122 is configured to perform beamforming techniques to steer its transmission of notification and data signals away from the mobile aerial participant 126 at a particular direction and in a particular pattern, which creates the corresponding coverage area 124. Although the coverage areas 124a-124d are illustrated in two dimensions, embodiments are not so limited and each coverage area 124a-124d may include three dimensional space. Moreover, each coverage area 124 may include a single beamwidth transmission or multiple separate beamwidth transmissions, such as discussed above in conjunction with FIGS. 4A-4B, which may be focused in specific directions away from the mobile aerial participant 126. In some embodiments, sensors 122a-122d may be configured to only scan a particular area away from the mobile aerial participant 126. In the illustrated example, sensors 122a-122d do not provide complete sensor coverage around mobile aerial participant 126, which demonstrates that efficiencies can be gained by integrating or deconflicting sensor coverage provided by other mobile aerial participants, as discussed herein.

Figure 6A:
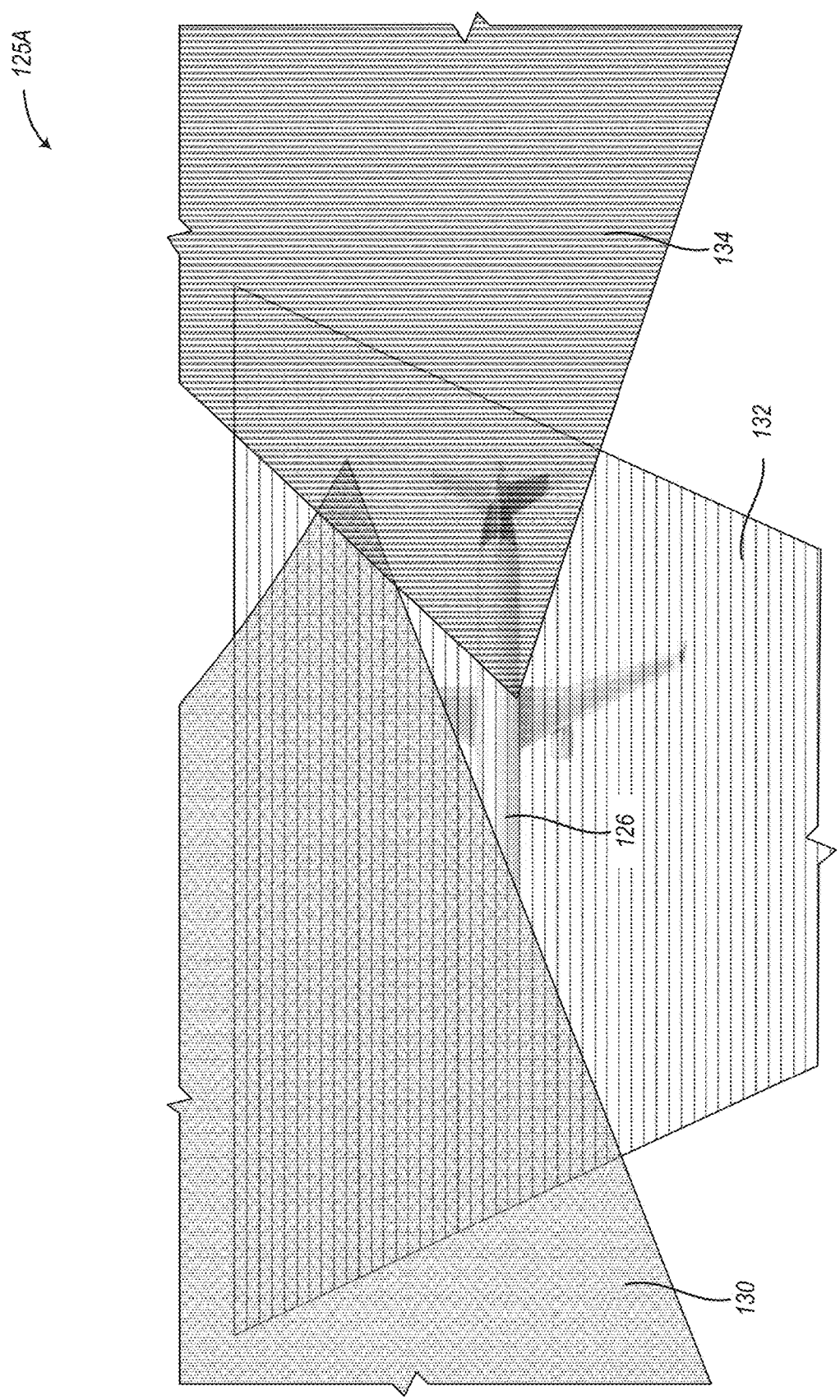

FIGS. 6A-6E illustrates context diagrams illustrating a use-case example of utilizing directional sensors along with sensor coverage management in accordance with embodiments described herein. Example 125A in FIG. 6A illustrates sensor coverage areas 130, 132, and 134 as being provided by sensors on other mobile aerial participants (not illustrated). Although not illustrated, the sensor coverage areas begin at sensors on other participants, but at least partially overlap an area around the mobile aerial participant 126. However, the sensor coverage areas 130, 132, and 134 do not provide complete coverage for mobile aerial participant 126, which is illustrated in FIG. 6B.

Example 125B in FIG. 6B illustrates the missing sensor coverage areas 140, 142, and 144, such that if these areas can be covered by sensors on the mobile aerial participant 126 or by other mobile aerial participants (not illustrated), then that coverage, along with the coverage areas 130, 132, and 134 would provide complete coverage for mobile aerial participant 126 to deconflict nearby objects (e.g., within a predetermined combination of velocity and distance).

Figure 6C:
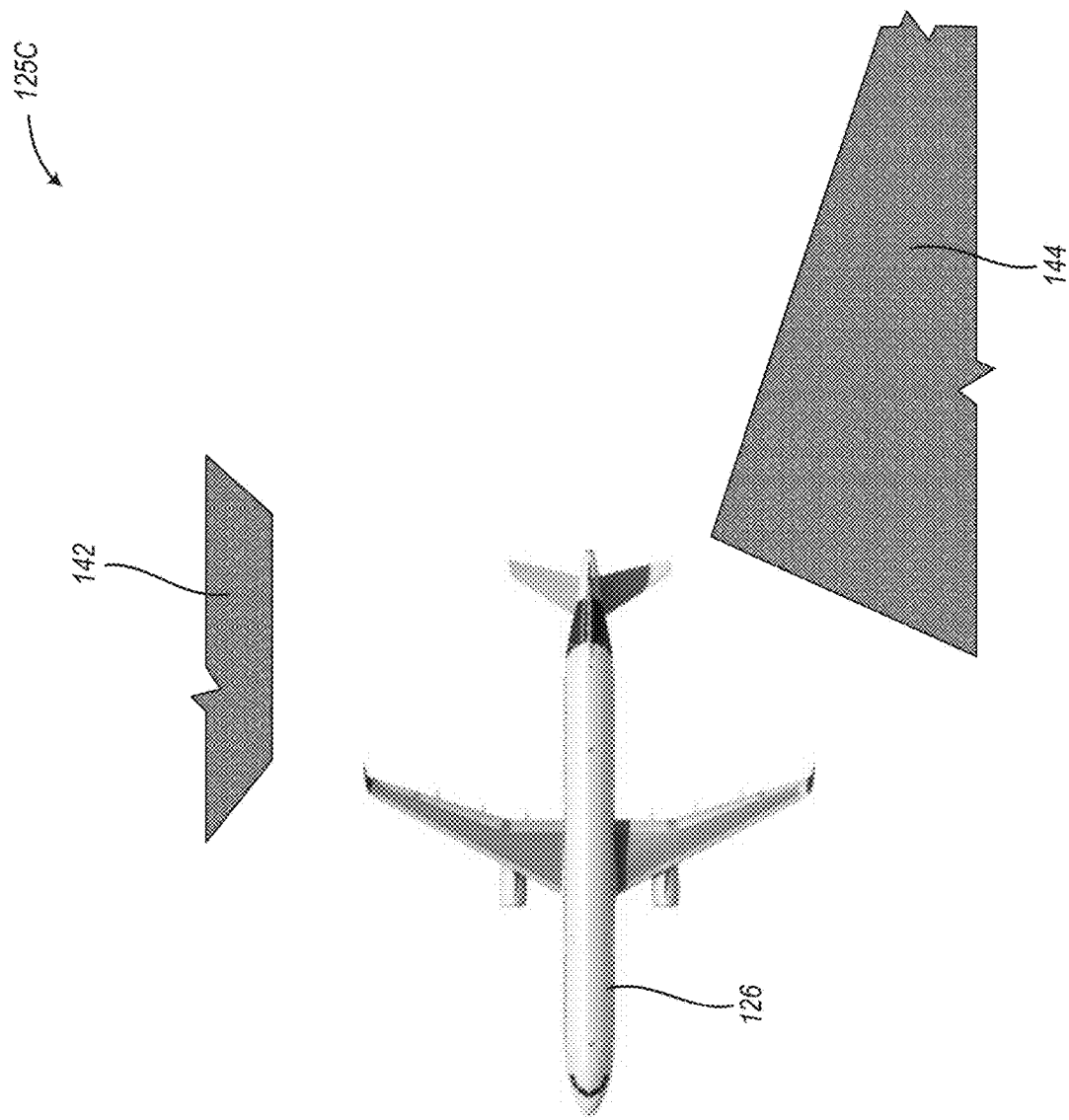
Figure 6D:
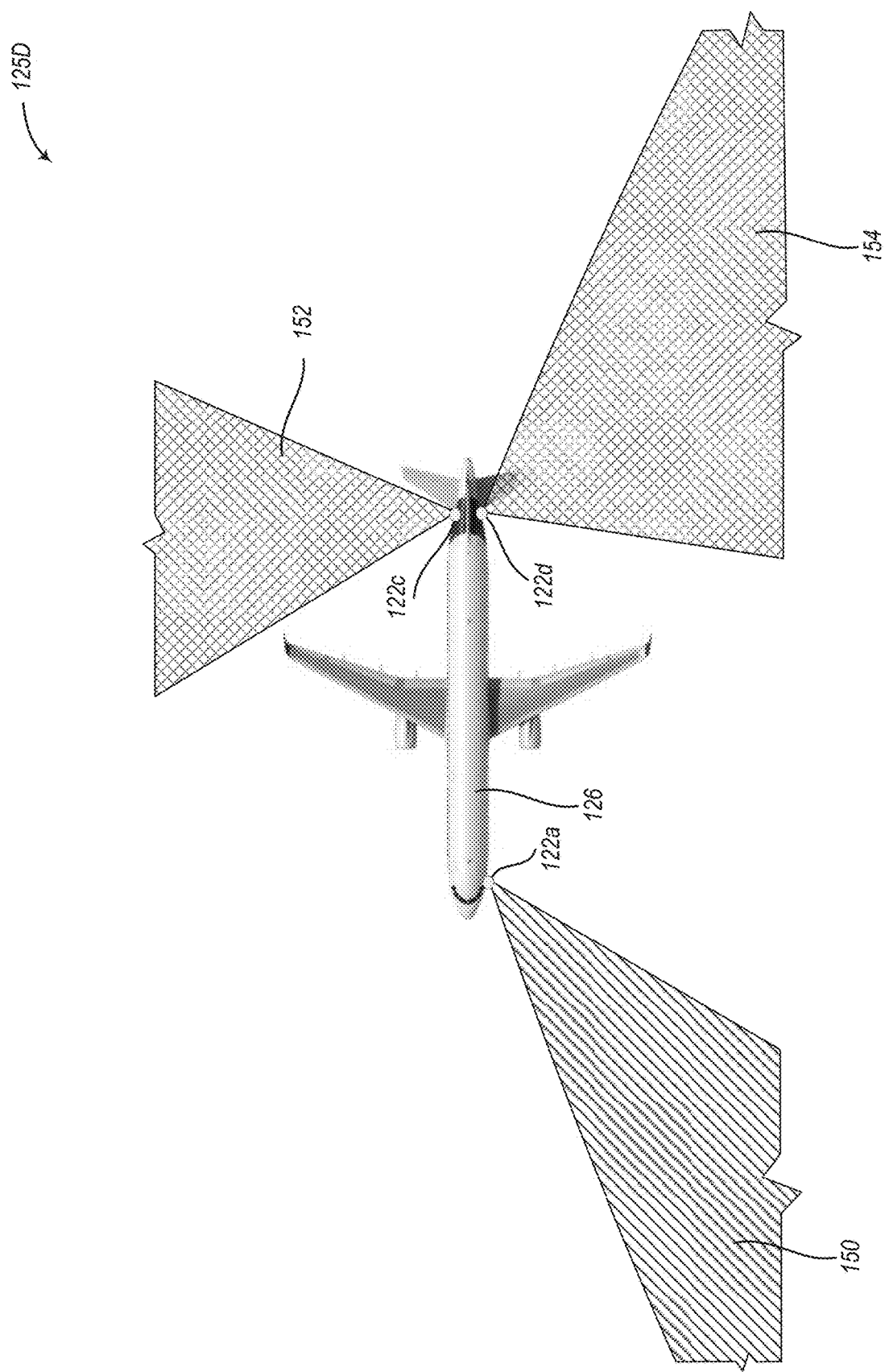

Example 125C in FIG. 6C illustrates the missing sensor coverage areas 140, 142, and 144 around mobile aerial participant 126. The mobile aerial participant 126 can then modify the transmission beamform of sensors 122a, 122c, and 122d to provide new coverage areas 150, 152, and 154 that overlap the missing sensor coverage areas 140, 142, and 144, which is shown by example 125D in FIG. 6D.

Figure 6E:
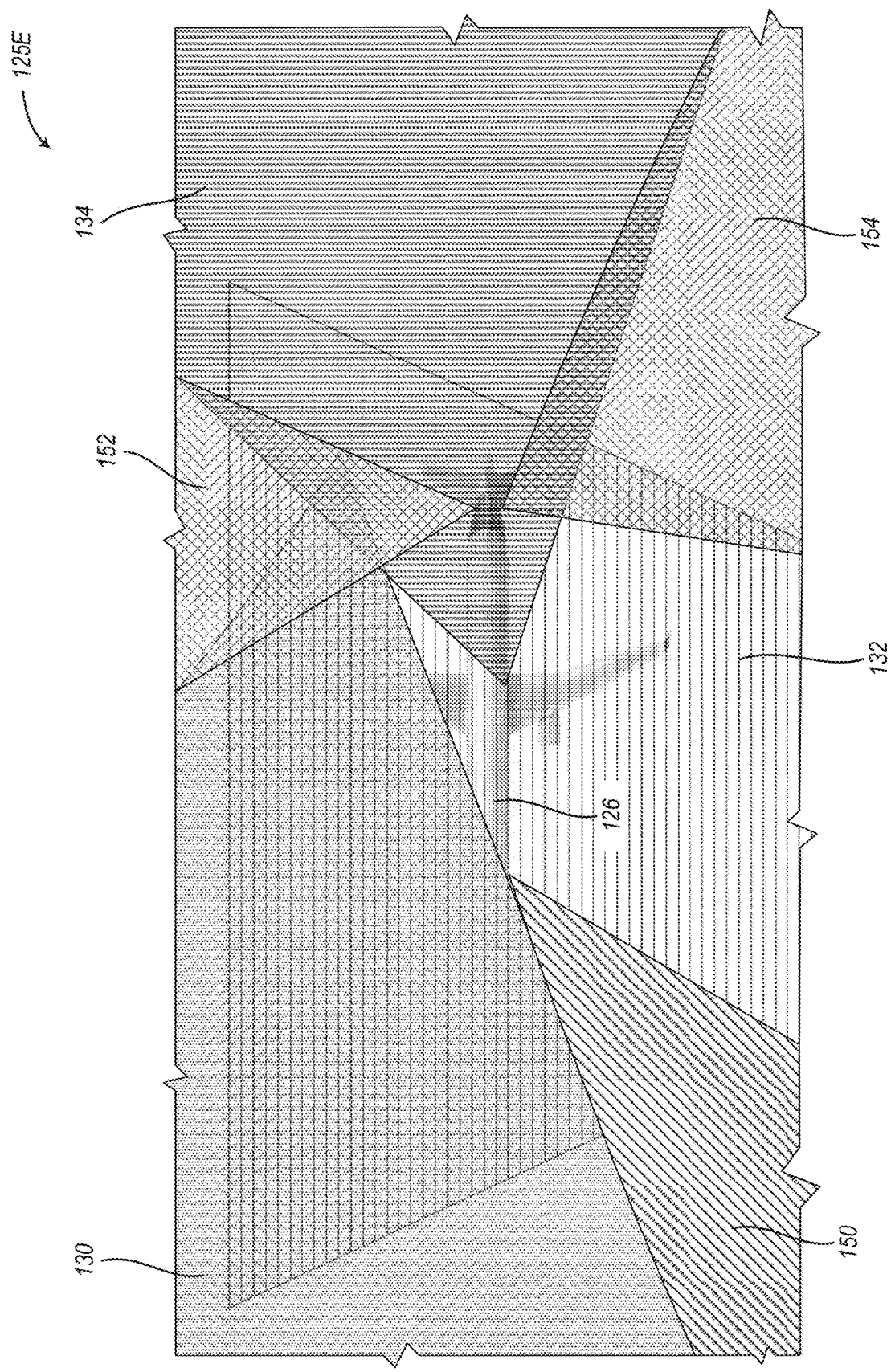

The newly positioned coverage areas 150, 152, and 154 provided by the sensors on the mobile aerial participant 126, along with the coverage areas 130, 132, and 134 provided by other sensors of other participants, provide complete coverage to deconflict nearby objects, which is illustrated by example 125E in FIG. 6E.

As mentioned herein, the coverage area may encompass three-dimensional airspace. The three-dimensional evaluation of airspace/coverage areas of sensors on a plurality of participants allows unwanted redundancy and inefficiencies (e.g., too many overlapping sensors) to be reduced, while improving total coverage area and redundancy when needed (e.g., partially overlapping sensor coverage areas to confirm detected objects). Thresholds for coverage area, detection, identification, and tracking allow the participants to act as a system-of-systems to work together, by passing notification signals, to meet thresholds or to deconflict objects to maximize coverage and network health.

Notification signals may contain transmit angle and beam characteristics that allow participants within the network to calculate the coverage area of each participant. In this way, each participant can locally calculate and manage their sensors in relation to the coverage areas provided by other participants within their line-of-sight. Notification signals may also be broadcast, transmitted, or forwarded to stationary participants or the network operations center to allow stationary participants to determine the management plan and communicate sensor coverage area adjustments back to mobile aerial participants.

As one example, a first mobile aerial participant to meet the threshold requirements for a given coverage area (for a given area, for the complete network, for individual participants, or some combination thereof) will continue to provide that coverage unless another participant has more coverage area. If the coverage area provided by the first mobile aerial participant does not meet at least one coverage area threshold for either an individual participant or the network, then one or more additional mobile aerial participants are instructed to utilize their sensors to provide additional coverage. More and more sensors or participants will be utilized to provide coverage until the thresholds are met or a maximum possible coverage area is achieved based on the number of participants, location of participants, and technical capabilities of the participants.

In various embodiments, the altitude of mobile aerial participants may also be utilized to determine how sensor coverage areas of a plurality of mobile aerial participants are utilized. For examples, mobile aerial participants that are flying at a higher altitude may deconflict higher altitudes, whereas mobile aerial participants that are flying a lower altitude may deconflict lower altitudes. In this way, if mobile aerial participants have overlapping coverage areas, their coverage areas can be adjusted to different altitudes to provide additional coverage volume thresholds. Both mobile aerial participants can then manage their scan pattern and refresh rate to maximize their data throughput while maintaining tracking and coverage thresholds.

Although many embodiments are described herein with respect to mobile aerial participants, embodiments are not so limited. For example, embodiments described herein may be implemented by mobile ground participants or a combination of mobile and stationary participants. The coverage volumes and thresholds set of each individual participant or network of participants may be set for each given type of participant. For example, cars will have a coverage area that envelopes the roadway and shoulders of the road they are on. Trains will cover the tracks and crossing intersections. Planes will cover the area in front of each plane required to ensure deconfliction as well as surrounding airspace with thresholds set by FAA, DHS, DoD and NOAA in the form of active airspaces, NOTAM, TFRs, advisories, etc. Moreover, such thresholds may dynamically change based on the velocity of the participants, the distance between participants, the number of participants in a given area, etc., or a combination thereof.

The operation of certain aspects will now be described with respect to FIG. 7. In at least one of various embodiments, processes 200 described in conjunction with FIG. 7 may be implemented by or executed on one or more computing devices, such as mobile participants 36, stationary participants 34, or network operation center 40.

Figure 7:
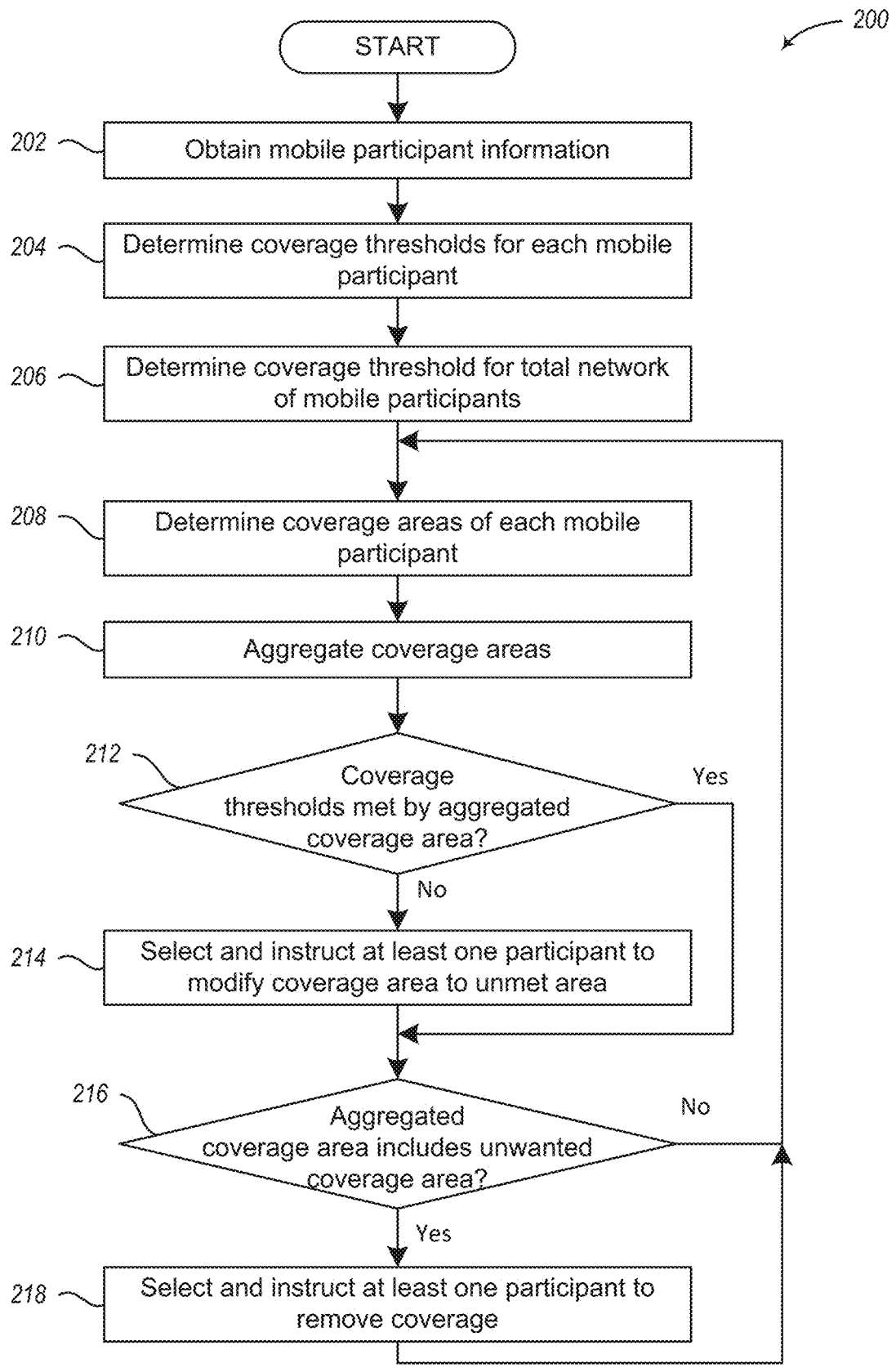
FIG. 7 illustrates a logical flow diagram showing one embodiment of an overview process for a computing system to provide sensor coverage management in accordance with embodiments described herein.

FIG. 7 illustrates a logical flow diagram showing one embodiment of an overview process for a computing system to provide sensor coverage management in accordance with embodiments described herein. Process 200 begins, after a start block, at block 202, where mobile participant information is obtained for each of a plurality of participants. In various embodiments, the participant information may include identification information, owner, type of participant, geolocation, kinematic information, throughput capabilities, frequency capabilities, number and locations of sensors and antennas, maximum sensor coverage areas, etc.

Process 200 proceeds to block 204, where individual coverage thresholds are determined for each mobile participant. In some embodiments, an individual threshold for a mobile participant may be identified as an area in one or more directions surrounding the mobile participant in which to monitor for possible threats to the mobile participant or to otherwise provide safety processing and support (e.g., to communicate with other participants, reduce the likelihood that the mobile participant may collide with another participant or object, etc.). In various embodiments, each individual coverage threshold may be determined based on the location and velocity of the participant, the type of participant, the maneuverability of the participant, etc.

Process 200 continued at block 206, where an overall network coverage threshold is determined. In some embodiments, the overall network coverage threshold may identify a given airspace/physical location and area, a plurality of participants, altitude coverage requirements, etc.

Process 200 proceeds next to block 208 to determine the current coverage area of each participant. In some embodiments, each participant may report what their current coverage area is based on its sensors current configuration. In other embodiments, the current coverage areas may be determined based on the number of sensors, their capabilities, and their position on their corresponding participant to determine what sensor coverage area is possible or currently being used by each participant.

Process 200 continues next at block 210, where the coverage areas are aggregated to identify overlapping and missing coverage areas.

Process 200 proceeds to decision block 212, where a determination is made whether the individual and network coverage thresholds are met by the aggregated coverage area. In some embodiments, this determination is based on a comparison between each threshold and the aggregated coverage area. A match between a particular threshold and the aggregated coverage area indicates that that particular threshold is met. If at least one threshold is not met, then process 200 flows to block 214; otherwise, process 200 flows to decision block 216.

At block 214, at least one participant is selected and instructed to modify at least one of its sensors to provide a modified coverage area. This modified coverage area is a coverage area that at least partially includes the coverage area missing from the aggregated coverage area for the particular unmet threshold.

Process 200 proceeds next at decision block 216, where a determination is made whether the aggregated coverage area includes unwanted coverage area. In various embodiments, this determination is based on a comparison between each coverage area in the aggregated coverage area to determine if there are overlapping coverage areas that may be redundant and inefficient. If there are unwanted coverage areas, then process 200 proceeds to block 218; otherwise, process 200 loops to block 204 to continue to dynamically update coverage areas to identify missing or unwanted coverage areas.

At block 218, at least one participant is selected and instructed to modify at least one of its sensors to provide a less coverage area or a coverage area that is different than the unwanted coverage area. After block 218, process 200 loops to block 204 to continue to dynamically update coverage areas to identify missing or unwanted coverage areas.

Figure 8:
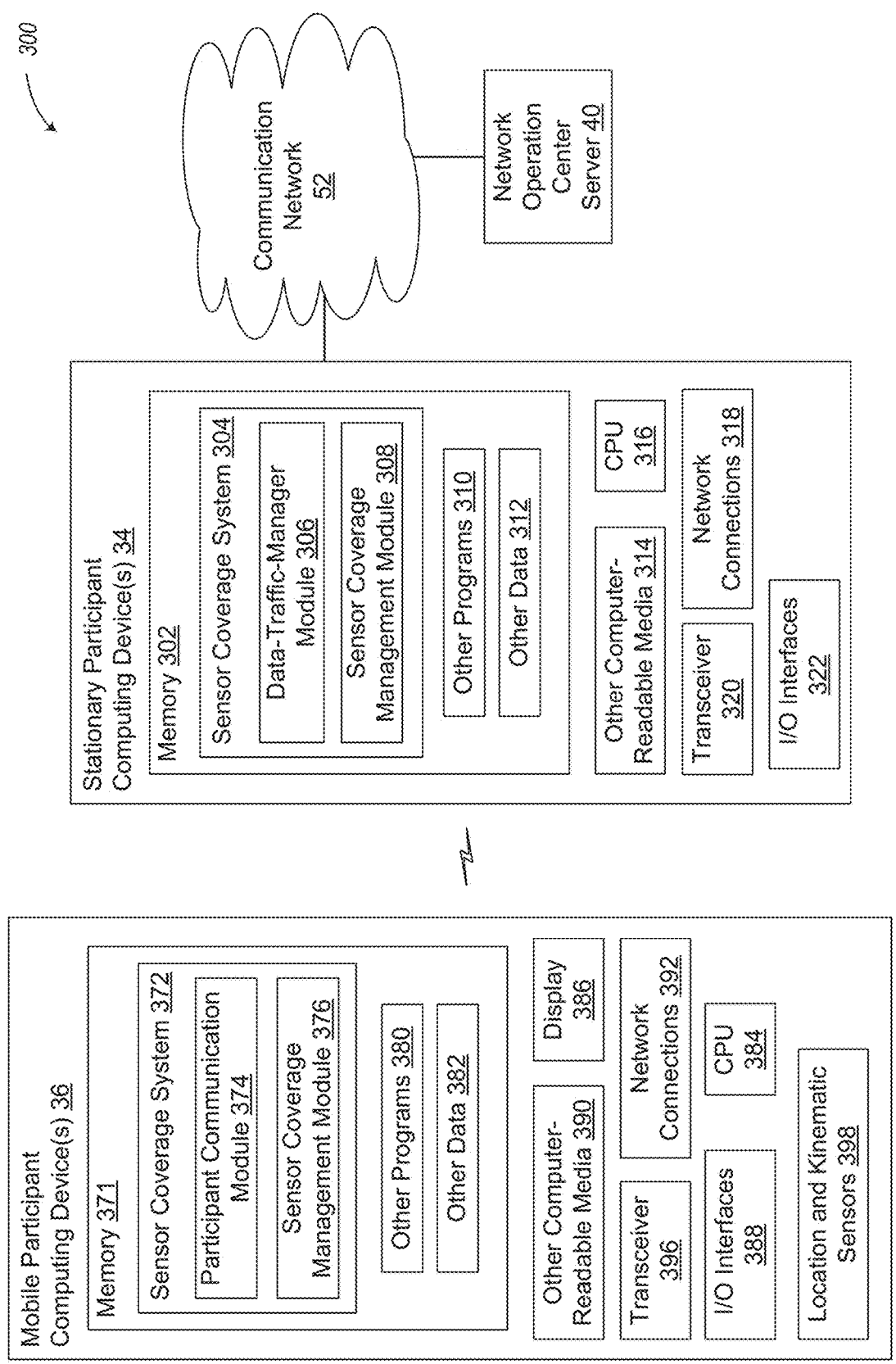
FIG. 8 shows a system diagram that describes one implementation of computing systems for implementing embodiments described herein

FIG. 8 shows a system diagram that describes one implementation of computing systems for implementing embodiments described herein. System 300 includes mobile participant computing device(s) 36, stationary participant computing device(s) 34, and network operation center server 40.

Mobile participant computing device(s) 36 communicate with one or more other mobile participant computing devices 36 and stationary participant computing devices 34 via line-of-sight communications to transmit data and other communications among the participants. One or more special-purpose computing systems may be used to implement each mobile participant computing device 36. Accordingly, various embodiments described herein may be implemented in software, hardware, firmware, or in some combination thereof. A mobile participant computing device 34 may include memory 371, one or more central processing units (CPUs) 384, display 386, I/O interfaces 388, other computer-readable media 390, network connections 392, transceiver 396, and motion sensors or other sensors 398.

Memory 371 may include one or more various types of non-volatile and/or volatile storage technologies. Examples of memory 371 may include, but are not limited to, flash memory, hard disk drives, optical drives, solid-state drives, various types of random access memory (RAM), various types of read-only memory (ROM), other computer-readable storage media (also referred to as processor-readable storage media), or the like, or any combination thereof. Memory 371 may be utilized to store information, including computer-readable instructions that are utilized by CPU 384 to perform actions, including embodiments described herein.

Memory 371 may have stored thereon sensor coverage system 372, which includes participant communication module 374, and optionally sensor coverage management module 376. The participant communication module 374 may employ embodiments described herein to send notification signals, track participants, track non-participants, and to generate and transfer data and communications to other participants. The sensor coverage management module 376 may employ embodiments described herein to receive sensor information from other participants and to identify a coverage area of the current sensors of participants in the network or in a given area. The sensor coverage management module 376 may also determine which sensors on which participants can be adjusted to modify their coverage area to reduce unwanted overlap, increase overlap to provide redundant coverage areas, or increase total coverage area. The sensor coverage management module 376 may then send information to other participants instructing them to modify their sensors accordingly.

The memory 371 may also store other programs 380 and other data 382. The other programs 380 may include user applications, other tracking or geo-positioning programs, etc. The other data 382 may include participant and sensor information, data or information regarding one or more non-participant objects, or other information.

Network connections 392 are configured to communicate with other computing devices, such as other mobile participant computing devices 36 and stationary participant computing devices 34 via transceiver 396 and line-of-sight communications mechanisms and technologies. Transceiver 396 may be a omni-directional transceiver that sends and receives radio signals independent of direction, or transceiver 396 may be a directional transceiver that sends or receives, or both sends and receives, radio signals to or from a particular direction relative to the positioning of the mobile participant computing device 36.

Location and kinematic sensors 398 include one or more sensors that are used to determine the position of the mobile participant computing device 36 and the kinematic information of how the mobile participant computing device 36 is moving. Examples of location and kinematic data sensors 398 include, but are not limited to using participant's self-reported notifications calibrated off of stationary participants, processing the echo of own self-reported notifications, GPS modules, accelerometers, gyroscopes, or other sensors that can be used to determine the position and kinematic information of the mobile participant computing device 36.

Other I/O interfaces 388 may include a keyboard, audio interfaces, video interfaces, or the like. Other computer-readable media 390 may include other types of stationary or removable computer-readable media, such as removable flash drives, external hard drives, or the like. Display 386 is a display interface that is configured to output images, content, or information to a user. Examples of display 386 include, but are not limited to, LCD screens, LEDs or other lights, or other types of display devices.

Stationary participant computing device(s) 34 communicate with mobile participant computing devices 36 via line-of-sight communications and with other stationary participants either by wired or wireless communications to transmit information or data to other participants or to non-participants. One or more special-purpose computing systems may be used to implement each stationary participant computing device 34. Accordingly, various embodiments described herein may be implemented in software, hardware, firmware, or in some combination thereof. A stationary participant computing device 34 may include memory 302, one or more central processing units (CPUs) 316, I/O interfaces 322, other computer-readable media 314, network connections 318, and transceiver 320.

Memory 302 may include one or more various types of non-volatile and/or volatile storage technologies. Examples of memory 302 may include, but are not limited to, flash memory, hard disk drives, optical drives, solid-state drives, various types of random access memory (RAM), various types of read-only memory (ROM), other computer-readable storage media (also referred to as processor-readable storage media), or the like, or any combination thereof. Memory 302 may be utilized to store information, including computer-readable instructions that are utilized by CPU 316 to perform actions, including embodiments described herein.

Memory 302 may have stored thereon sensor coverage system 304, which includes data-traffic-manager module 306, and optionally sensor coverage management module 308. The data-traffic-manager module 306 may be configured to transfer data from one participant to another participant and to manage and provide participant information updates. In various embodiments, data-traffic-manager module 306 may communicate with network operation center server 40 via communication network 52, such as to provide or receive participant information updates. The sensor coverage management module 308 may perform embodiments similar to sensor coverage management module 376 to track and manage sensor coverage area of the network.

The memory 302 may also store other programs 310 and other data 312. The other data 312 may include participant data or information, data or information regarding one or more tracked objects, or other information.

Network connections 318 are configured to communicate with other computing devices, such as other stationary participant computing devices 34 and mobile participant computing devices 36 via transceiver 320 and wired or line-of-sight communications mechanisms and technologies. Network connections 318 are also configured to communicate with the network operation center server 40 via communication network 52.

Transceiver 320 may be a omni-directional transceiver that sends and receives radio signals independent of direction, or transceiver 320 may be a directional transceiver that sends or receives, or both sends and receives, radio signals to or from a particular direction relative to the position of the stationary participant computing device 34.

Other I/O interfaces 314 may include a keyboard, audio interfaces, video interfaces, or the like. Other computer-readable media 314 may include other types of stationary or removable computer-readable media, such as removable flash drives, external hard drives, or the like.

Network operation center server 40 includes one or more computing devices that store information about the positioning of mobile participant computing devices 36 and stationary participant computing devices 34, such as a master participant table. The network operation center server 40 may also store information regarding the sensor capabilities of each participant, as described herein. The network operation center server 40, in some embodiments, performs embodiments similar to sensor coverage management module 376. The network operation center server 40 also includes memory, one or more processors, network interfaces and connections, and other computing components similar to mobile participant computing devices 36 and stationary participant computing devices 34, but those components are not shown here for ease of illustration.

Communication network 52 may include one or more wired or wireless communication networks to transmit data between one stationary participant computing device 34 and another stationary participant computing device 34 or with the network operation center server 40.

The various embodiments described above can be combined to provide further embodiments. These and other changes can be made to the embodiments in light of the above-detailed description. Moreover, additional details and use case examples are provided in the U.S. patents, U.S. patent application publications, U.S. patent applications, foreign patents, foreign patent applications and non-patent publications referred to in this specification and/or listed in the Application Data Sheet, including but not limited to U.S. patent application Ser. No. 15/892,259, filed Feb. 8, 2018, entitled "Object Tracking Using A Cognitive Heterogeneous Ad Hoc Mesh Network;" Provisional Patent Application No. 62/467,572, filed Mar. 6, 2017, entitled "Scatternet: A cognitive heterogeneous ad hoc mesh data/cellular/Wi-Fi network establishment/access points/connected devices through utilization of software applications exploiting existing technologies and frequency spectrum for data and voice communications through the exploitation of the Internet and Internet of Things, resulting in the creation of Data communications Adaptive RADAR (DATAR);" and U.S. patent application Ser. No. 15/913,612, filed Mar. 6, 2018, entitled "Cognitive Heterogeneous Ad Hoc Mesh Network;" which are incorporated herein by reference, in their entirety.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method comprising:
   determining, by a participant computing device, a current individual coverage area for a plurality of mobile participants;
   aggregating, by the participant computing device, the current individual coverage areas of the plurality of mobile participants;
   determining, by the participant computing device, if the aggregated current coverage area meets an individual coverage threshold for the plurality of mobile participants and a network coverage threshold across the plurality of mobile participants; and
   in response to the aggregated current coverage area not meeting at least one individual coverage threshold or the network coverage threshold:
      determining, by the participant computing device, a missing coverage area based on a comparison between the aggregated current coverage area and the at least one individual coverage threshold or the network coverage threshold not met by the aggregated current coverage area; and
      instructing, by the participant computing device, a target mobile participant of the plurality of mobile participants to modify the current individual coverage area of the target mobile participant to at least partially overlap the missing coverage area.

2. The method of claim 1, wherein instructing the target mobile participant to modify the current individual coverage area of the target mobile participant includes:
   modifying a sensor coverage area of at least one sensor on the target mobile participant.

3. The method of claim 1, wherein the participant computing device is a computing device of one of the plurality mobile participants.

4. The method of claim 1, wherein the participant computing device is a computing device of the target mobile participant.

5. The method of claim 1, wherein determining the current individual coverage area for the plurality of mobile participants includes:
   determining, by the participant computing device, a current sensor coverage area for a plurality of sensors that are mounted on the plurality of mobile participants.

6. The method of claim 1, wherein determining the current individual coverage area for the plurality of mobile participants includes:
   determining, by the participant computing device, a three-dimensional sensor coverage area around each of the plurality of mobile participants.

7. The method of claim 1, wherein instructing the target mobile participant to modify the current individual coverage area of the target mobile participant includes:
   determining, by the participant computing device, a current processing capacity of the target mobile participant and; and
   identifying, by the participant computing device, a coverage area that at least partially overlaps the missing coverage area for the target mobile participant based on the determined current processing capacity.

8. The method of claim 1, wherein instructing the target mobile participant to modify the current individual coverage area of the target mobile participant includes:
   instructing, by the participant computing device, the target mobile participant to modify a transmission beamform of at least one sensor mounted on the target mobile participant to provide a new coverage area that overlaps a portion of the missing coverage area.

9. The method of claim 1, further comprising:
   in response to the aggregated current coverage area including at least one unwanted overlapping coverage area, instructing, by the participant computing device, another target mobile participant of the plurality of mobile participants to modify the current coverage area of the other target mobile participant to remove at least a portion of an unwanted overlapping coverage area.

10. A computing device, comprising
    a memory that stores computer instructions; and
    a processor that executes the computer instruction to:
       determine an aggregation of current individual coverage areas for a plurality of mobile aerial participants;
       determine if the aggregated current coverage area meets an individual coverage threshold for each separate mobile aerial participant of the plurality of mobile aerial participants and a network coverage threshold across the plurality of mobile aerial participants; and
       in response to the aggregated current coverage area not meeting at least one individual coverage threshold or the network coverage threshold:
          determine a missing coverage area based on a comparison between the aggregated current coverage area and the at least one individual coverage threshold or the network coverage threshold not met by the aggregated current coverage area; and instruct a mobile aerial participant of the plurality of mobile participants to modify the current individual coverage area of the mobile aerial participant to at least partially overlap the missing coverage area.

11. The computing device of claim 10, wherein the processor instructs the mobile aerial participant to modify the current individual coverage area of the mobile aerial participant by further executing the computer instructions to:
modify a sensor coverage area of at least one sensor on the mobile aerial participant.

12. The computing device of claim 10, wherein the processor determining the current individual coverage area for the plurality of mobile aerial participants by further executing the computer instructions to:
determine a current sensor coverage area for a plurality of sensors that are mounted on the plurality of mobile aerial participants.

13. The computing device of claim 10, wherein the processor determining the current individual coverage area for the plurality of mobile aerial participants by further executing the computer instructions to:
determine a three-dimensional sensor coverage area around each of the plurality of mobile aerial participants.

14. The computing device of claim 10, wherein the processor instructing the mobile aerial participant to modify the current individual coverage area of the mobile aerial participant by further executing the computer instructions to:
determine a current processing capacity of the mobile aerial participant and; and
identify a coverage area that at least partially overlaps the missing coverage area for the mobile aerial participant based on the determined current processing capacity.

15. The computing device of claim 10, wherein the processor instructing the mobile aerial participant to modify the current individual coverage area of the mobile aerial participant by further executing the computer instructions to:
instruct the mobile aerial participant to modify a transmission beamform of at least one sensor mounted on the mobile aerial participant to provide a new coverage area that overlaps a portion of the missing coverage area.

16. The computing device of claim 10, wherein the processor further executes the computer instructions to:
in response to the aggregated current coverage area including at least one unwanted overlapping coverage area, instruct another mobile aerial participant of the plurality of mobile aerial participants to modify the current coverage area of the other mobile aerial participant to remove at least a portion of an unwanted overlapping coverage area.

17. A non-transitory computer-readable storage medium that stores instructions that, when executed by a processor in a computing system, cause the processor to perform actions, the actions comprising:

determining an individual coverage area for a plurality of mobile aerial participants;

aggregating the individual coverage areas of the plurality of mobile aerial participants;

determining if the aggregated coverage area meets an individual coverage threshold for the plurality of mobile aerial participants and a network coverage threshold across the plurality of mobile aerial participants; and in response to the aggregated coverage area not meeting at least one individual coverage threshold or the network coverage threshold:
determining a missing coverage area based on a comparison between the aggregated coverage area and the at least one individual coverage threshold or the network coverage threshold not met by the aggregated coverage area; and
instructing a target mobile aerial participant of the plurality of mobile participants to modify the individual coverage area of the target mobile aerial participant to at least partially overlap the missing coverage area.

18. The non-transitory computer-readable storage medium of claim 17, wherein execution of the instructions by the processor to instruct the target mobile aerial participant to modify the individual coverage area of the target mobile aerial participant, cause the processor to perform further actions, the further actions comprising:
determining a processing capacity of the target mobile aerial participant and; and
identifying a coverage area that at least partially overlaps the missing coverage area for the target mobile aerial participant based on the determined processing capacity.

19. The non-transitory computer-readable storage medium of claim 17 wherein execution of the instructions by the processor to instruct the target mobile aerial participant to modify the individual coverage area of the target mobile aerial participant, cause the processor to perform further actions, the further actions comprising:
instructing the target mobile aerial participant to modify a transmission beamform of at least one sensor mounted on the target mobile aerial participant to provide a new coverage area that overlaps a portion of the missing coverage area.

20. The non-transitory computer-readable storage medium of claim 17, wherein execution of the instructions by the processor, cause the processor to perform further actions, the further actions comprising:
in response to the aggregated coverage area including at least one unwanted overlapping coverage area, instructing another target mobile aerial participant of the plurality of mobile aerial participants to modify the coverage area of the other target mobile aerial participant to remove at least a portion of an unwanted overlapping coverage area.

* * * * *